United States Patent
Ujihara et al.

(10) Patent No.: US 9,034,796 B2
(45) Date of Patent: May 19, 2015

(54) METHOD FOR ANALYSIS USING NUCLEIC ACID MICROARRAY

(75) Inventors: Dai Ujihara, Kanagawa (JP); Hideyuki Kanehara, Kanagawa (JP); Johji Inazawa, Tokyo (JP); Issei Imoto, Tokyo (JP)

(73) Assignees: FUJIFILM Corporation, Tokyo (JP); National University Corporation Tokyo Medical and Dental University, Tokyo (JP)

( * ) Notice: Subject to any disclaimer, the term of this patent is extended or adjusted under 35 U.S.C. 154(b) by 984 days.

(21) Appl. No.: 12/994,718

(22) PCT Filed: May 27, 2009

(86) PCT No.: PCT/JP2009/060098
§ 371 (c)(1),
(2), (4) Date: Dec. 30, 2010

(87) PCT Pub. No.: WO2009/145346
PCT Pub. Date: Dec. 3, 2009

(65) Prior Publication Data
US 2011/0105357 A1    May 5, 2011

(30) Foreign Application Priority Data

May 27, 2008  (JP) ................................. 2008-138533
May 26, 2009  (JP) ................................. 2009-126780

(51) Int. Cl.
*C12Q 1/68* (2006.01)
*G01N 33/58* (2006.01)

(52) U.S. Cl.
CPC ............ *C12Q 1/6837* (2013.01); *G01N 33/582* (2013.01)

(58) Field of Classification Search
None
See application file for complete search history.

(56) References Cited

U.S. PATENT DOCUMENTS

| | | | |
|---|---|---|---|
| 2004/0132080 A1 | 7/2004 | Kawaguchi et al. |
| 2005/0153290 A1 | 7/2005 | Van Beuningen |
| 2008/0120038 A1 | 5/2008 | Ghosh et al. |

FOREIGN PATENT DOCUMENTS

| | | | |
|---|---|---|---|
| EP | 1522853 A1 | 4/2005 |
| EP | 1722309 A1 | 11/2006 |
| JP | 2004-28695 A | 1/2004 |

(Continued)

OTHER PUBLICATIONS

Peixoto et al. (BMC Genomics, 2006, 7(35):1-12).*

(Continued)

*Primary Examiner* — Christopher M Babic
*Assistant Examiner* — Jeremy C Flinders
(74) *Attorney, Agent, or Firm* — Birch, Stewart, Kolasch & Birch, LLP

(57) ABSTRACT

An analytical method aided with a nucleic acid microarray, the nucleic acid microarray having a spot (X 1) onto which a first probe nucleic acid is immobilized, the method includes: allowing a labeled sample nucleic acid (A 1) of a sample to be tested to hybridize with the first probe nucleic acid; providing the spot (X 1) with a labeled verification nucleic acid (B) that has a sequence capable of hybridizing with at least a part of the first probe nucleic acid and is labeled with a label different from the labeled sample nucleic acid (A 1), and allowing the labeled verification nucleic acid (B) to hybridize with at least the first probe nucleic acid at all spots; measuring a labeled quantity value (F 1) of the labeled sample nucleic acid (A 1); and measuring a labeled quantity value (Fc 1) of the labeled verification nucleic acid (B).

14 Claims, 10 Drawing Sheets

NUCLEIC ACID MICROARRAY 1

NUCLEIC ACID MICROARRAY 2

(56) References Cited

FOREIGN PATENT DOCUMENTS

| WO | 02/052038 A2 | 7/2002 |
|---|---|---|
| WO | 2007/097876 A2 | 8/2007 |

OTHER PUBLICATIONS

Cai et al. (Nat. Biotech., 2002, 20:393-396).*
Williams et al. (Nucleic Acids Research, 2004, vol. 32, No. 10 e81, pp. 1-10).*
Imoto et al., "Analysis of copy number aberrations using array-based comparative genomic hybridization: CGH-array analysis", Cell Engineering, vol. 23, No. 3, 2004, pp. 355-361.
Inazawa et al., "CGH Array and its application preparation of x-chromosome CGH array and its practical application", Clinical Inspection, vol. 49, No. 5, May 2005, pp. 497-502.
Office Action issued on Dec. 6, 2012 in corresponding European patent application No. 09 754 854.9.
Chinese Office Action for Application No. 200980128809.X dated Aug. 21, 2012.
Written Opinion of the International Searching Authority dated Feb. 16, 2010, for International Application No. PCTJP2009/060098.
Chinese Office Action issued on May 16, 2013 in corresponding Chinese Patent Application No. 200980128809.X.
Albertson et al., "Genomic microarrays in human genetic disease and cancer", Human Molecular Genetics, 2003, vol. 12, Review Issue 2, Oct. 15, 2003, pp. R145-R152, XP002295535, ISSN: 0964-6906.
Dudley et al., "Measuring absolute expression with microarrays with a calibrated reference sample and an extended signal intensity range", Proceedings of the National Academy of Sciences of USA, National Academy of Science, Washington, DC, US, vol. 99, No. 11, May 28, 2002, pp. 7554-7559, XP002338318 ISSN: 0027-8424.
Forozan et al., "Comparative Genomic Hybridization Analysis of 38 Breast Cancer Cell Lines: A Basis for Interpreting Complementary DNA Microarray Data", Cancer Research, American Association for Cancer Research, Baltimore, MD, US, vol. 60, No. 16, Aug. 15, 2000, pp. 4519-4525, XP002304931 ISSN: 0008-5472.
International Search Report dated Feb. 16, 2010 for PCT/JP2009/060098.
Mantripragada et al., "Genomic microarrays in the spotlight", Trends in Genetics, vol. 20, No. 2, Feb. 2004, pp. 87-94, XP004486426, ISSN: 0168-9525.
Patterson et al., "Performance comparison of one-color and two-color platforms within the MicroArray Quality Control (MAQC) project", Nature Biotechnology, Nature Publishing Group, New York, US, vol. 24, No. 9, Sep. 1, 2006, pp. 1140-1150, XP002538562, ISSN: 1087-0156.
Pinkel et al., "High resolution analysis of DNA copy number variation using comparative genomic hybridization to microarrays", Nature Genetics, Nature Publishing Group, New York, US, vol. 20, Oct. 1, 1998, pp. 207-211, XP002925115, ISSN: 1061-4036.
Wessendorf et al, "Automated screening for genomic Imbalances using Matrix-based Comparative Genomic Hybridization", Laboratory Investigation, United States and Canadian Academy of Pathology, Inc. vol. 82, No. 1, pp. 47-60, 2002, XP-002537229, ISSN: 0023-6837.
Japanese Office Action for corresponding Japanese Application No. 2009-126780 dated Oct. 8, 2013 (with partial English translation).
Japanese Office Action issued in Japanese Patent Application No. 2009-126780 on Aug. 5, 2014, with English translation.
Cai et al., "Genome-wide detection of chromosomal imbalances in tumors using BAC microarrays", Nature Biotechnology, vol. 20 (2002) pp. 393-396.
European Office Action issued in European Patent Application No. 09 754 854.9 on Jul. 30, 2014.
Peixoto et al., "Evaluation of reference-based two-color methods for measurement of gene expression ratios using spotted cDNA microarrays", BMC Genomics, vol. 7, No. 35 (2006) 12 pages.

* cited by examiner

NUCLEIC ACID MICROARRAY 1

NUCLEIC ACID MICROARRAY 2

NO CORRECTION

CORRECTED

FIG. 7A
FIG. 7B
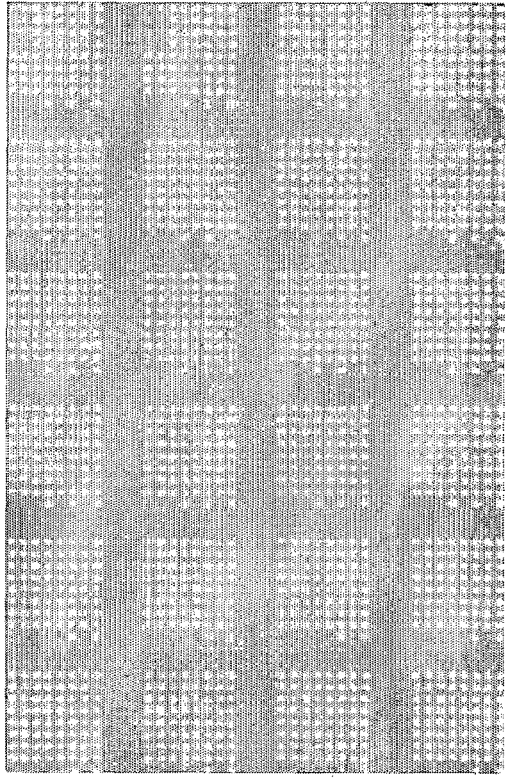
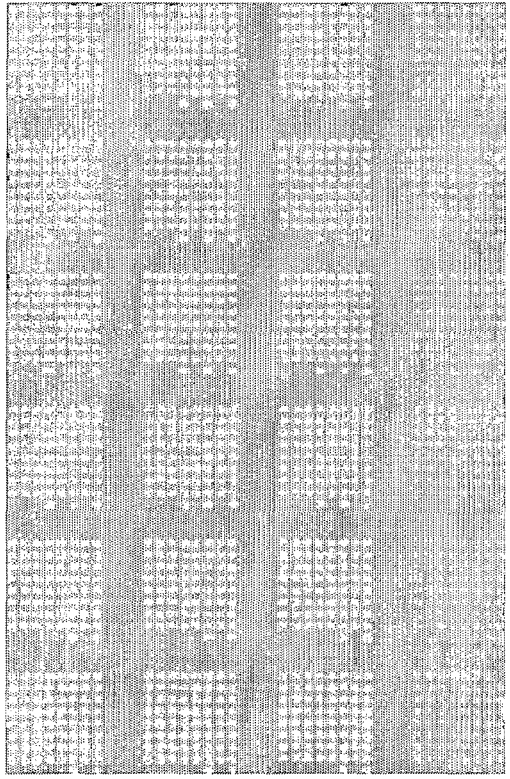

NO CORRECTION BY CORRECTING NUCLEIC ACID

CORRECTION BY CORRECTING NUCLEIC ACID

CORRECTION BY LABELED CORRECTING NUCLEIC ACID

CORRECTION IN THE CASE OF USING INCREASED AMOUNT OF LABELED CORRECTING NUCLEIC ACID

CORRECTION BETWEEN ARRAYS 1

CORRECTION BETWEEN ARRAYS 2

A CASE OF NOT CARRYING OUT CORRECTION BETWEEN ARRAY 1 AND ARRAY 2

CORRECTION BETWEEN ARRAY 1 AND ARRAY 2

METHOD FOR ANALYSIS USING NUCLEIC ACID MICROARRAY

TECHNICAL FIELD

This invention relates to a method for increasing reliability of measured values in the analysis which uses a nucleic acid microarray.

BACKGROUND ART

As a method for detecting excess, deletion, amplification and the like abnormal copy numbers of genomic DNA using chromosomes as the object, there is a genomic CGH method which has been developed by Joe Gray, Dan Pinkel, O-P Kallioniemi et al. In general, there were various problems in that a chromosomal aberrancy cannot be detected except that it is within a large region covering from 5 to 10 Mb or more, skills are required for the analysis, and the like (J. Inazawa and M. Minaguchi, Rinsho Kensa (Clinical Inspection), 49, 497-502 (2005)).

There is an array CGH method as a tool which can detect a genomic structure aberrancy occurred at a level of from several 10 kb to several Mb, higher than the resolution that can be analyzed by chromosomal analyses (D. Pinkel et al., Nat. Genet., 20, 207-211 (1998) and I. Imoto and J. Inazawa, Saibo Kogaku (Cell Engineering), 23, 355-361 (2004)). The array CGH method uses an array in which fragments of genomic DNA, such as BAC (bacterial artificial chromosomes) clones, YAC (yeast artificial chromosomes) clones, PAC (P1-derived artificial chromosomes) or DNAs or oligonucleotides prepared based on these BAC, YAC, PAC and the like, are arranged on a solid substrate by spotting them on the substrate. In addition, this is a method for detecting relative numbers of copies of genes, by extracting target DNA samples from an abnormal cell to be used as a sample to be tested collected from a patient or the like and a normal cell to be used as a standard sample collected from a healthy person, labeling them with respectively different labels (fluorescent materials or the like), allowing them to simultaneously contact with a probe on the nucleic acid microarray, thereby allowing them to undergo interaction via hybridization, reading off fluorescence signals generated from the interacted target nucleic acids using a scanner or the like, and comparing intensity ratios of the signals of the normal cell- and abnormal cell-derived target nucleic acids.

When a sample and a standard are labeled with respectively different labeling compounds and allowed to hybridize with a nucleic acid microarray in carrying out an analysis which uses the nucleic acid microarray, the difference in data caused by different spots (spotted amount or the like) or the like or by a difference in hybridization, generated between batches of the microarray, hardly occurs. However, since the labeling is different, a difference in labeling efficiency, a difference in the detection system for individual labeling, and the like are apt to exert influence on the result, and it accompanies a complexity of always requiring preparation of the standard for one sample to be tested. In order to exclude the difference in labeling, the problem does not occur when a method is employed in which the standard and sample to be tested are labeled with the same labeling compound and allowed to undergo hybridization separately with two or more nucleic acid arrays, and the evaluation is carried out between them. However, a problem is generated by this method, in which the data fluctuation due to difference in spot once resolved by simultaneously carrying out the hybridization is again generated in carrying out separate labeling. As a method for solving these problems, there is a method in which a difference between arrays is corrected by newly mounting a spot for correction and internal standard use on the microarray, but it cannot correct the difference between separate spots (e.g., JP-A-2004-028695).

SUMMARY OF INVENTION

The problem that the invention is to solve is to provide a method which can simultaneously solve a problem of a method for labeling a sample to be tested and a standard using two species or more labels, in which a difference between the labels exerts influence on data, and a problem in which a difference between individual spots exerts influence on date when a sample to be tested and a standard are labeled using one species of label, in carrying out a measuring method which uses a nucleic acid microarray.

As one of the measures for improving accuracy of data when a nucleic acid microarray measurement is carried out using one label, there is a strategy in which a difference between arrays is suppressed as low as possible by synthesizing an oligonucleotide probe on the arrays like the case of GeneChip, a difference in hybridization between arrays is suppressed as low as possible by designing the sequence in such a manner that the so-called Tm value of the probe becomes equivalent, and a difference in the labeling step is also suppressed by arranging a correcting spot, but the correcting method is complex and it is particularly difficult to carry out the comparison by such a strategy in the case of nucleic acid microarrays having two or more sequences for one spot (e.g., JP-A-2004-028695).

Accordingly, it was found by the invention that a difference between spots of probe nucleic acid can be detected when a nucleic acid having substantially the same binding ability in all of the spots on an array and on similar spots between different arrays, namely a verification nucleic acid having a sequence capable of hybridizing with at least a part of the probe nucleic acid on all of the spots, is allowed to coexist with a sample to be detected and a standard, and binding amount of the verification nucleic acid is detected by respectively carrying out hybridization. In addition, it was able to correct a difference between spots using the binding amount as an index, thus resulting in the accomplishment of the invention.

For example, hybridization is carried out on the first plate of array by allowing a standard labeled with Cy 3 and a verification nucleic acid labeled with Cy 5 to coexist. On the other hand, on the second plate of array, a mixture of a sample to be tested labeled with Cy 3 and the verification nucleic acid labeled with Cy 5 is hybridized with a probe nucleic acid on the array. When a difference is found by comparing the standard and sample to be tested, it is possible to eliminate a difference between spots by carrying out its correction using the verification nucleic acid.

In this case, it is desirable that the verification nucleic acids labeled with Cy 5 are nucleic acids having identical sequence, and it is desirable that their preparation is identical. In addition, as the method for correcting a difference between spots, it may be any calculation method with the proviso that the correction can be theoretically made using any calculation method. Preferably, the standard and sample to be tested are compared by calculating ratios of fluorescence values of the standard and sample to be tested using a fluorescence value obtained from the verification nucleic acid.

It is desirable to add the labeled verification nucleic acid and the standard and sample to be tested to the same solution and concentrate volume of the solution by ethanol precipitation method or the like, and even when it cannot be carried out, it is desirable to concentrate the nucleic acid concentration as high as possible.

That is, the invention consists of the following constructions.

(1) An analytical method aided with a nucleic acid microarray, the nucleic acid microarray having a spot (X 1) onto which a first probe nucleic acid is immobilized, the method comprising:

allowing a labeled sample nucleic acid (A 1) of a sample to be tested to hybridize with the first probe nucleic acid immobilized onto the spot (X 1);

providing the spot (X 1) with a labeled verification nucleic acid (B) that has a sequence capable of hybridizing with at least a part of the first probe nucleic acid and is labeled with a label different from the labeled sample nucleic acid (A 1), and allowing the labeled verification nucleic acid (B) to hybridize with at least the first probe nucleic acid at all spots;

measuring a labeled quantity value (F 1) of the labeled sample nucleic acid (A 1) hybridized on the spot (X 1); and measuring a labeled quantity value (Fc 1) of the labeled verification nucleic acid (B) hybridized on the spot (X 1).

(2) The analytical method as described in (1) above, wherein the allowing of the labeled sample nucleic acid (A 1) to undergo hybridization and the allowing of the labeled verification nucleic acid (B) to undergo hybridization are simultaneously carried out, and the measuring of an amount of the hybridized labeled sample nucleic acid (A 1) and the measuring of an amount of the hybridized verification nucleic acid (B) are simultaneously carried out.

(3) The analytical method as described in (1) or (2) above, wherein an amount of the first probe nucleic acid immobilized onto the spot (X 1) is detected based on the labeled quantity value (Fc 1), and the labeled quantity value (F 1) is corrected based on the detected amount.

(4) The analytical method as described in any one of (1) to (3) above, further comprising:

providing a spot (X n) onto which an $n^{th}$ probe nucleic acid having substantially the same sequence of the first probe nucleic acid immobilized onto the spot (X 1) with a labeled sample nucleic acid (A n) which is identical to or different from the labeled sample nucleic acid (A 1), and allowing the labeled sample nucleic acid (A n) to hybridize with the $n^{th}$ probe nucleic acid immobilized onto the spot (X n), the spot (X n) being present on the same nucleic acid microarray of the spot (X 1) or an another nucleic acid microarray;

providing the spot (X n) with the labeled verification nucleic acid (B), and allowing the labeled verification nucleic acid (B) to hybridize with at least the $n^{th}$ probe nucleic acid;

measuring a labeled quantity value (F n) of the labeled sample nucleic acid (A n) hybridized on the spot (X n); and measuring a labeled quantity value (Fc n) of the labeled verification nucleic acid (B) hybridized on the spot (X n).

(5) The analytical method as described in (4) above, further comprising:

calculating a coefficient of the labeled quantity values at the spot (X 1) and spot (X n) by comparing the labeled quantity values (Fc 1) and (Fc n).

(6) The analytical method as described in (4) or (5) above, wherein the labeled sample nucleic acid (A 1) and labeled sample nucleic acid (A n) are prepared by labeling nucleic acids obtained from different samples.

(7) The analytical method as described in any one of (1) to (6) above, wherein an un-labeled nucleic acid identical to the same species of the labeled verification nucleic acid (B) before combining with a labeling compound is further added to the hybridization of the labeled verification nucleic acid (B).

(8) The analytical method as described in any one of (4) to (7) above, wherein a corrected labeled quantity value which corresponds to a hybridized amount of the labeled sample nucleic acid (A n) on the spot (X n) is calculated by using the following formula (1):

corrected labeled quantity value of the labeled sample nucleic acid (A n)=the labeled quantity value (Fc 1)/the labeled quantity value (Fc n)×the labeled quantity value (F n) of the $n^{th}$ labeled sample nucleic acid (A n) (n is an integer of 2 or more)　　　formula (1).

(9) The analytical method as described in any one of (1) to (8) above, wherein at least one labeling of the labeled sample nucleic acid (A 1) and labeled verification nucleic acid (B) is effected by fluorescence.

(10) The analytical method as described in any one of (1) to (9) above, wherein a BAC-DNA microarray is used as the nucleic acid microarray.

(11) The analytical method as described in any one of (1) to (10) above, wherein two or more of the same species of the spots (X n) are present in different nucleic acid microarrays, and arrangement of the $n^{th}$ probe nucleic acid and spotting amounts of the $n^{th}$ probe nucleic acid between respective nucleic acid microarrays are different in respective nucleic acid microarrays.

(12) The analytical method as described in any one of (1) to (11) above, wherein a nucleic acid which is different from a nucleic acid of the sample and has a sequence on the first and $n^{th}$ probe nucleic acids is used as the labeled verification nucleic acid (B).

(13) The analytical method as described in any one of (1) to (12) above, wherein a nucleic acid containing a repeated sequence is used as the labeled verification nucleic acid (B).

(14) The analytical method as described in any one of (1) to (13) above, wherein Cot-1 DNA is used as the labeled verification nucleic acid (B).

(15) The analytical method as described in any one of (1) to (12) above, wherein a vector-derived nucleic acid is used as the labeled verification nucleic acid (B).

(16) The analytical method as described in any one of (1) to (15) above, wherein the labeled quantity value (Fc 1) among the labeled quantity values (F 1) and (Fc 1) is supplied by digital data.

(17) A program causing a computer to execute a process for the analytical method as described in any one of (5) to (16) above, the process comprising:

correcting the labeled quantity value (F n) of the $n^{th}$ labeled sample nucleic acid (A n) (n is an integer of 2 or more) based on the labeled quantity value (Fc 1) and labeled quantity value (Fc n) of the labeled verification nucleic acid (B).

(18) A computer-readable medium storing a program causing a computer to execute a process for the analytical method as described in any one of (5) to (16) above, the process comprising:

correcting the labeled quantity value (F n) of the $n^{th}$ labeled sample nucleic acid (A n) (n is an integer of 2 or more) based on the labeled quantity value (Fc 1) and labeled quantity value (Fc n) of the labeled verification nucleic acid (B).

(19) A method for calculating gene expression quantities between samples or numbers of gene copies between samples, by using the analytical method as described in any one of (1) to (16) above.

(20) A kit for the analytical method as described in any one of (1) to (16) above, the kit comprising:

a nucleic acid microarray having a plurality of spots onto each of which a probe nucleic acid is immobilized; and a verification nucleic acid that has a sequence capable of hybridizing with at least respective parts of the probe nucleic acids at all spots on the nucleic acid microarray.

BRIEF DESCRIPTION OF DRAWINGS

FIGS. 7A and 7B are an example of a case in which a bias was formed in the fluorescence value. FIG. 7A is an image drawing after a nucleic acid microarray test of Cy 3-Female and Cy 5-Cot-1, and FIG. 7B is an image drawing after a nucleic acid microarray test of Cy 3-Male and Cy 5-Cot-1;

DESCRIPTION OF EMBODIMENTS

Figure 1:
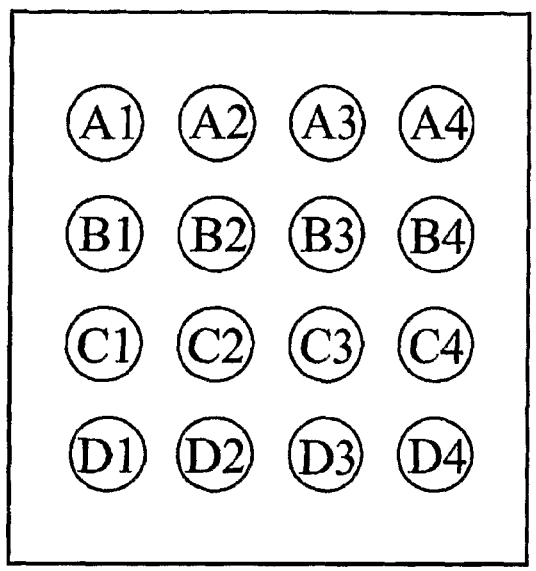
FIG. 1 is a schematic illustration of the principle of the invention. In the schematic illustration, only a case in which kind of the sample-derived labeled sample nucleic acid is two species was shown for the sake of simplification. In addition, the number of spots was shown by simplifying it to 16 spots per nucleic acid microarray. The A1 to A4 and a1 to a4 show substantially the same probe nucleic acids. Hereinafter, a group of B1 to B4 and b1 to b4, a group of C1 to C4 and c1 to c4 and a group of D1 to D4 and d1 to d4 respectively show the same probe nucleic acids.
Figure 1:
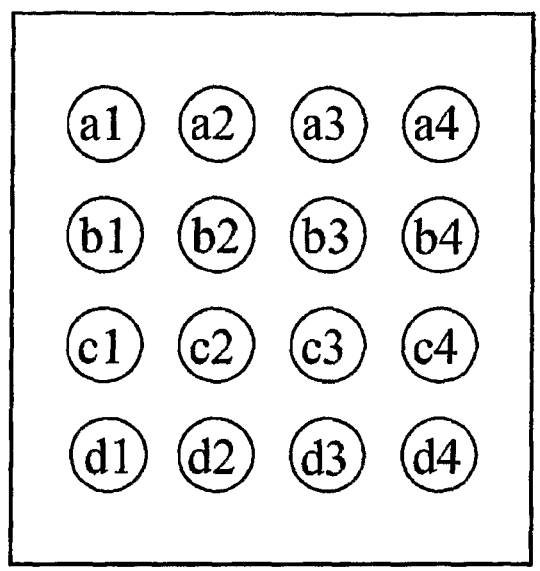

The invention relates to a method for analyzing nucleic acid using a nucleic acid microarray, characterized in that said nucleic acid microarray has a spot (X 1) onto which a first probe nucleic acid comprising a prove sequence (a') complementary to a sequence (a) is immobilized, and that it comprises a step for allowing a labeled sample nucleic acid (A 1) of a sample to be tested to hybridize with at least said first probe nucleic acid immobilized onto the spot (X 1), a step for providing the spot (X 1) with, and thereby allowing it to hybridize with, a labeled verification nucleic acid (B) which has a sequence capable of hybridizing with at least a part of the first probe nucleic acid and is labeled with a label different from the aforementioned labeled sample nucleic acid, at all spots, a step for measuring a labeled quantity value (F 1) of said labeled sample nucleic acid hybridized on the spot (X 1), and a step for measuring a labeled quantity value (Fc 1) of said labeled verification nucleic acid (B) hybridized on the spot (X 1).

The above-mentioned analytical method is preferably a nucleic acid analyzing method for examining a nucleic acid having a sequence (a) in a sample to be tested (A) using a nucleic acid microarray, characterized in that said nucleic acid microarray has a spot (X 1) onto which a first probe nucleic acid comprising at least one or more of a sequence (a') complementary to the (a) is immobilized, and that it comprises a step for allowing a sample nucleic acid (A 1) prepared by labeling (A) and a verification nucleic acid (B) having a sequence capable of hybridizing with at least a part of the first probe nucleic acid, at all spots, to hybridize with said first probe nucleic acid immobilized onto the spot (X 1), in the coexistence of a nucleic acid (B 1) labeled with a label which is different from (A), a step for further allowing a nucleic acid (C 1) prepared by labeling a standard (C) with the same label of (A) to coexist with (B 1) and to hybridize with said probe nucleic acid immobilized onto a spot (X 1') having the same sequence of the spot (X 1), a step for measuring a labeled quantity value (Fa 1) of said labeled sample nucleic acid hybridized on the spot (X 1), a step for measuring a labeled quantity value (Fb 1) of said labeled verification nucleic acid (B) hybridized on the spot (X 1), a step for measuring a labeled quantity value (Fc 1) of a nucleic acid comprising said sequence (c) hybridized on the spot (X 1'), and a step for measuring a labeled quantity value (Fb 1') of said labeled verification nucleic acid (B) hybridized on the spot (X 1').

While amount of the sequence (a) to be detected and the labeled quantity value (Fc 1) at (X 1') are compared to carry out the measurement by only the labeled quantity value (Fa 1) on an optional spot (X 1), use of the labeled quantity value (Fb 1, Fb 1') of labeled verification nucleic acid (B) for the correction renders possible detection of an error at said spot, such as an error caused by the amount of the probe nucleic acid immobilized on the spot.

When this labeled quantity value of labeled verification nucleic acid (B) is used, an abnormality of said spot can be judged for example from its comparison with the designed value of (Fc 1), an error between spots can be detected by verifying labeled quantity value of the labeled verification nucleic acid (B) among two or more spots, and it also becomes possible to correct the error.

The invention can use a nucleic acid array in which preferably a probe nucleic acid having two or more sequences is spotted on one position.

According to the invention, amount of a sample nucleic acid (A) can be ascertained, further preferably, by using a solution containing (A) of a sample to be tested and a verification nucleic acid (B) having a sequence capable of hybridizing with at least a part of the probe nucleic acid, at all spots, for one array as the hybridization solution containing nucleic acids, subsequently carrying out an array test using a standard nucleic acid (C) and the labeled verification nucleic acid (B) for another array, correcting labeled quantity value of (A) and labeled quantity value of (C) using labeled quantity value of the thus detected labeled verification nucleic acid (B), and comparing the labeled quantity value of (A) with the labeled quantity value of (C). In this connection, the another array means the same kind of array, namely an array on which the same kind of probe is spotted.

In this case, the spots as the objects of carrying out comparison and correction are not particularly limited, but it is desirable that these are the same kind of spots (spots prepared by spotting the same probe, that is, spots having the same sequence (a') as the object of the immobilized probe nucleic acid).

By the invention, a change in the labeled quantity value caused by a difference in the amount of probe nucleic acid and a difference in the hybridization can for example be corrected. In this connection, when the term "labeled quantity value" is used in the invention, it includes a labeled amount obtained from a complex generated by the hybridization of a labeled nucleic acid and a probe nucleic acid, such as a labeling compound of a double-stranded nucleic acid or the like.

Regarding the step for detecting labeled amounts of a labeled sample nucleic acid (A) and a labeled verification nucleic acid (B), by allowing the labeled sample nucleic acid (A) and labeled verification nucleic acid (B) to undergo hybridization, through the application of a hybridization solution containing the labeled sample nucleic acid (A) and labeled verification nucleic acid (B), prepared by labeling respective nucleic acids, to the spots on the microarray, more illustratively, it is desirable that it comprises the following steps (a) to (e).

(a) A step for obtaining the labeled sample nucleic acid (A) by labeling a nucleic acid with a labeling compound.

(b) A step for obtaining the labeled verification nucleic acid (B) by labeling a verification nucleic acid containing a sequence capable of hybridizing with at least a part of the probe nucleic acid, at all spots, with a labeling compound which is different from the step (a), (c) A step for preparing a hybridization solution containing the labeled sample nucleic acid (A) obtained in the step (a) and the labeled verification nucleic acid (B) obtained in the step (b).

(d) A step for applying the hybridization solution obtained in the step (c) onto the nucleic acid microarray and thereby allowing the labeled sample nucleic acid (A) and labeled verification nucleic acid (B) in the hybridization solution to hybridize with the probe nucleic acid.

(e) A step for reading respective amounts of the labeled sample nucleic acid (A) and labeled verification nucleic acid (B) hybridized with the probe nucleic acid and thereby obtaining labeled quantity values.

In this connection, it is desirable to further include, between the step (d) and step (e), a step for washing the hybridized array with a washing liquid.

Also, in adding the labeled sample nucleic acid (A) and labeled verification nucleic acid (B) in the step (c), these may be added simultaneously or separately.

In addition, it can further include the following steps.

(a") A step for obtaining a labeled standard nucleic acid (C).

(c") A step for preparing a hybridization solution containing the labeled standard nucleic acid (C) and the labeled verification nucleic acid (B) obtained in the above-mentioned step (b).

(d") A step for carrying out hybridization with an array which is the same kind but different from the aforementioned step (d).

(e") A step for obtaining respective labeled quantity values of the labeled standard nucleic acid (C) and labeled verification nucleic acid (B) hybridized in the aforementioned (d"), correcting (labeled quantity value of (A) and) labeled quantity value of (C) using labeled quantity value of the thus detected labeled verification nucleic acid (B), and ascertaining the amount of (A) by comparing labeled quantity value of (A) and labeled quantity value of (C).

The hybridization can be carried out using a commercially available instrument for carrying out hybridization or an instrument which can carry out temperature control alone. It is desirable to carry out the hybridization at a temperature of within the range of from 30° C. to 50° C., more preferably within the range of from 35° C. to 45° C.

In addition, it is desirable to set the hybridization time to from 16 to 100 hours, more preferably from 24 to 80 hours, further preferably from 40 to 72 hours.

After the hybridization, washing and the like are optionally carried out. Regarding the washing conditions, the washing effect becomes high as the frequency is increased, and it is possible to use a washing liquid having adjusted ionic strength, such as 2×SSC, 2×SSC/50% formamide, 2×SSC/ 0.1% SDS, 1×SSC or the like, or a dispersant, surfactant or the like washing liquid which is generally used in carrying out Southern blotting, northern blotting or the like hybridization experiment. Regarding the temperature, it is preferable to set it to a range of from 15° C. to 70° C., more preferably from 25° C. to 50° C., and it is necessary to adjust the solution volume to an equivalent level of the hybridization condition.

Preferred is a method for correcting labeled quantity values among spots prepared by spotting the same probe nucleic acid between nucleic acid microarrays or between hybridization regions, which comprises the following steps (1) or (1') and (2).

(1) A step for obtaining a nucleic acid microarray in which a labeled sample nucleic acid (A) and a labeled verification nucleic acid (B) are hybridized with a probe nucleic acid on the spot, by carrying out the following steps (a1) to (f1).

(a1) A step for obtaining the labeled sample nucleic acid (A) by labeling a sample nucleic acid with a labeling compound.

(b1) A step for obtaining a labeled verification nucleic acid (B) by labeling a verification nucleic acid containing a sequence capable of hybridizing with at least a part of the probe nucleic acid, at all spots, with a labeling compound which is different from the step (a) (the verification nucleic acid may be complementary to the sample nucleic acid), (c1) A step for preparing a hybridization solution containing the labeled sample nucleic acid (A) obtained in the step (a1) and the labeled verification nucleic acid (B) obtained in the step (b1).

(d1) A step for carrying out hybridization by applying the hybridization solution obtained in the step (c1) onto the nucleic acid microarray.

(e1) A step for washing the nucleic acid microarray obtained in the step (d1) with a washing liquid.

(f1) A step for reading respective amounts of the labeled sample nucleic acid (A) and labeled verification nucleic acid (B) hybridized with the probe nucleic acid, from the nucleic acid microarray obtained by the step (e1), and thereby obtaining labeled quantity values.

(1') A step for obtaining a nucleic acid microarray in which a labeled sample nucleic acid (A) and a labeled verification nucleic acid (B) are hybridized with a probe nucleic acid on the nucleic acid microarray, by carrying out the following steps (a1') to (g1').

(a1') A step for obtaining the labeled sample nucleic acid (A) by labeling a nucleic acid with a labeling compound.

(b1') A step for obtaining a labeled verification nucleic acid (B) by labeling a verification nucleic acid containing a sequence capable of hybridizing with at least a part of the probe nucleic acid, at all spots, with a labeling compound which is different from the step (a) (the verification nucleic acid may be complementary to the nucleic acid), (c1') A step for preparing a hybridization solution containing the labeled verification nucleic acid (B) obtained in the step (b1').

(d1') A step for preparing a hybridization solution containing a labeled sample nucleic acid (A) and a labeled verification nucleic acid (B), by mixing the labeled sample nucleic acid (A) obtained in the step (a1') and the labeled verification nucleic acid (B) obtained in the step (c1').

(e1') A step for carrying out hybridization by applying the solution obtained in the step (d1') onto the nucleic acid microarray.

(f1') A step for washing the nucleic acid microarray obtained by the step (e1') with a washing liquid.

(g1') A step for reading respective amounts of the labeled sample nucleic acid (A) and labeled verification nucleic acid (B) hybridized with the probe nucleic acid, from the nucleic acid microarray obtained by the step (f1'), and thereby obtaining labeled quantity values.

(2) A step for calculating the gene expression quantity between samples to be tested or the number of gene copies of a sample to be tested, by carrying out the step (1) or (1') for respective nucleic acids obtained from at least two samples to be tested, thereby obtaining nucleic acid microarrays corresponding to the number of kinds of the used samples to be tested, or hybridization regions corresponding to the number of kinds of the used samples to be tested, and correcting at least one kind among the labeled quantity values of the labeled sample nucleic acids (A) derived from the used samples to be tested by using the labeled quantity value of the labeled verification nucleic acid (B).

In this case, it is desirable that at least one of the samples to be tested is the above-mentioned standard (C) having known amount. By this, other samples to be tested can be measured more precisely.

In the labeled quantity value correction method of the invention, respective labeled quantity values are obtained by allowing a labeled sample nucleic acid (A1) and a labeled verification nucleic acid (B) to simultaneously hybridize with the first spot, and a probe nucleic acid identical to the aforementioned spot is spotted, but more illustratively, respective labeled quantity values are obtained by allowing a labeled standard nucleic acid (A n; n is an integer of 2 or more) which is deferent from the aforementioned labeled sample nucleic acid (A1), but is prepared with the aim of comparing labeled quantity value with the aforementioned labeled sample nucleic acid (A1), and a labeled verification nucleic acid (B) to simultaneously hybridize with the $n^{th}$ spot different from the aforementioned spot, ratio of the labeled quantity values of respective labeled verification nucleic acids (B) obtained by allowing to hybridize with the $1^{st}$ spot and the $n^{th}$ spot is used as the coefficient between said spots, and a corrected labeled quantity value of the labeled sample nucleic acid (A n) hybridized with the $n^{th}$ spot is obtained by multiplying the labeled quantity value of a labeled sample nucleic acid (A'), measured at said spot, by said coefficient.

It is able to calculate average value, or deviation from the average value, of at least one of the labeled quantity value of labeled sample nucleic acid (A) and labeled quantity value of labeled verification nucleic acid (B), among two or more spots where the same probe nucleic acid is spotted.

Illustratively, in the case of n spots (Xn) immobilized with a probe nucleic acid having the same sequence (a') identical to a spot (X1) presenting on the same nucleic acid array or different arrays, it is desirable to include a step for obtaining labeled quantity values of said labeled verification nucleic acids (B) hybridized with the n spots, by the method described in any one of the items (1) to (6) above and a step for calculating numerical values obtained by averaging, or deviating from the average value, of labeled quantity values of n numbers of said labeled verification nucleic acids (B).

More illustratively, when labeled quantity value of a labeled verification nucleic acid (B) obtained from the $1^{st}$ spot hybridized with a labeled sample nucleic acid (A1) derived from the $1^{st}$ sample to be tested and the labeled verification nucleic acid (B) is regarded as Fc 1, and labeled quantity values of a labeled sample nucleic acid (An) derived from the $n^{th}$ sample to be tested and the labeled verification nucleic acid (B) are regarded as Fc n, it is desirable to carry out the correction by calculating the corrected labeled quantity value after correction of the $n^{th}$ labeled sample nucleic acid (An) using the following numerical expression (1).

corrected labeled quantity value of the $n^{th}$ labeled sample nucleic acid (An)=Fc 1/Fc n×labeled quantity value of the $n^{th}$ labeled sample nucleic acid (An) (n is an integer of 2 or more)   Formula (1);

A principle of the invention is described using FIG. 1. In this connection, since this drawing is for describing a principle of the invention and therefore is very simplified, thus illustrating only the gist of the invention as an example, it does not include all of the above-mentioned scope of the invention, so that the invention is not limited by this drawing.

In FIG. 1, a schematic drawing was prepared for the sake of simplification by imagining, in the case of using nucleic acid microarrays for the analysis of the number of copies between two species of samples to be tested, two nucleic acid microarrays in which 4 probe sample nucleic acids (A to D or a to d) and identical probe nucleic acids 1 to 4 are spotted, in a total of 16 spots, on one array.

A mixture of a cell 1-derived labeled sample nucleic acid (A) as a sample to be tested, a labeled verification nucleic acid (B) and a hybridization solution is coated on a nucleic acid microarray 1 and allowed to undergo hybridization. Also, a mixture of a standard-derived labeled sample nucleic acid (A), the labeled verification nucleic acid (B) and a hybridization solution is coated on a nucleic acid microarray 2 and allowed to undergo hybridization. After the hybridization and subsequent washing and drying steps, labeled quantity value of both of the nucleic acid microarray 1 and nucleic acid microarray 2 is read off.

The labeled sample nucleic acid (A)-derived labeled quantity value for spot A1 on the nucleic acid microarray 1 is regarded as F 1, and the labeled verification nucleic acid (B)-derived labeled quantity value for the same spot A 1 as Fb 1. Also, the labeled sample nucleic acid (A)-derived labeled quantity value for spot a1 on the nucleic acid microarray 2 is regarded as F 2, and the labeled verification nucleic acid (B)-derived labeled quantity value for the same spot a1 as Fb 2. The corrected labeled quantity value F 2' after correction of the labeled sample nucleic acid (A)-derived labeled quantity value on the nucleic acid microarray 2 can be calculated, for example, by the following formula. In this case, a background labeled quantity value may be subtracted or not subtracted from the labeled quantity value.

$$F2'=Fb1/Fb2 \times F2$$

A result is obtained by carrying out this for all of the spots. That is, correction of all spots for the nucleic acid microarray 2 is carried out by carrying out correction of a group between spots to which a substantially identical prove nucleic acid is bonded, such as a group of the spot A2 on the nucleic acid microarray 1 and the spot a2 on the nucleic acid microarray 2, a group of the spot B1 on the nucleic acid microarray 1 and the spot b2 on the nucleic acid microarray 2, and the like. Next, a Ratio value between the nucleic acid microarray 1 and nucleic acid microarray 2 is calculated by the following formula.

$$Ratio=F2'/F1$$

When this is calculated for all groups of the spots, it becomes possible to obtain the number of copies.

In this connection, in carrying out the correction, it is also desirable to obtain a corrected labeled quantity value of the labeled sample nucleic acid (A), by using the ratio of a labeled quantity value of the labeled verification nucleic acid (B) of an optional spot to the average of labeled quantity values of labeled verification nucleic acid (B) measured on two or more of the same kind of spots, as a coefficient on said spots, and by dividing the labeled quantity value of the labeled sample nucleic acid (A) measured at said spots by said coefficient.

According to the invention, the spots to be corrected may be corrected for any spots with the proviso that they are spots to which substantially the same prove nucleic acid is bonded. For example, correction of positionally symmetric spots between nucleic acid microarrays, namely between the spots A1 and a1, spots B1 and b1 and the like of FIG. 1, can be cited. Also, correction of positionally asymmetric spots can also be carried out with the proviso that substantially the same probe nucleic acid is immobilized thereto.

In addition, according to the invention, correction between different nucleic acid microarrays can be carried out with the proviso that the probe nucleic acids are almost the same. The different nucleic acid microarray means a nucleic acid microarray produced for a different purpose or a nucleic acid microarray spotted in spots having different arrangement, shape or concentration.

That is, even when the arrangement of a probe nucleic acid or the spotting amount of the probe nucleic acid among two or more nucleic acid microarrays is different in each nucleic acid microarray, the evaluation can be carried out by correcting it by the method of the invention.

The labeled quantity value may be a value after carrying out a mathematical treatment. For example, the correction may be carried out after carrying out a step for averaging the labeled quantity values obtained from the spots prepared by spotting a substantially the same probe nucleic acid. In addition, it is desirable to use a fluorescence value as the labeled quantity value.

As the labeled quantity value, an average value calculated from the spots prepared by spotting a substantially the same probe nucleic acid can also be used. That is, an averaging treatment can be carried out on the labeled quantity values before correction. By the use of an average value, the data cone close to the true values. In addition, average value of labeled quantity values after correction can be calculated by the labeled quantity values obtained from the spots prepared by spotting a substantially the same probe nucleic acid. The averaging can also be carried out on the mathematical values obtained by processing the labeled quantity values after correction. When treated in this manner, for example, when an average value among spots prepared by spotting a substantially the same probe nucleic acid is calculated based on the Ratio value obtained by correcting a nucleic acid microarray, the data come close to the true values so that the number of copies can be calculated more accurately, thus rendering possible inhibition of the generation of so-called false positive and also rendering possible sharp improvement of accuracy of diagnosis and prevention of diseases.

In addition, an average value obtained by eliminating the maximum value and the minimum value in a group of substantially the same kind of probe nucleic acid can also be used, and a labeled amount of a spot in which a certain threshold value is eliminated from the average labeled amount of a probe nucleic acid group can also be used.

The correction of labeled quantity value can be carried out together with various control spots. For example, there is a method in which a housekeeping gene having a relatively constant expression quantity among cells is spotted on a nucleic acid microarray in advance, entire portion of the samples is corrected based on its hybridized amount, and then correction of each spot is carried out using the verification nucleic acid of the invention. In addition, by adding an internal standard nucleic acid at the time of amplification or labeling in advance, correction of each spot by the verification nucleic acid of the invention may be carried out after correcting the amplification or labeling with the internal standard nucleic acid.

According to the invention, correction among three or more nucleic acid microarrays is also possible. For example, a case in which two or more species of standard and sample to be tested are prepared can be cited. More illustratively, quantities can be calculated by obtaining data on the labeled quantity value of a labeled sample nucleic acid as the standard and labeled quantity value of a labeled verification nucleic acid and on the labeled quantity values of respective two or more samples to be tested and labeled quantity values of verification nucleic acids, correcting labeled quantity values of respective samples to be tested and labeled quantity value of the standard using the method of the invention, and then comparing labeled quantity values of the standard and respective samples to be tested. By carrying out such a method, when only one kind of a result of a standard-aided nucleic acid microarray is prepared in advance, many kinds of nucleic acid microarray which uses samples to be tested as the target can be carried out, and it is not necessary to prepare a step for labeling the standard in equivalent numbers of the species of samples to be tested so that the number of steps can be reduced in that degree and the testing period of time and diagnosing period of time can also be shortened. Also, necessary amounts of reagents can be sharply decreased, and accompanied by this, the cost can be sharply reduced. In addition, the results can be further clarified by using two or more species of standard.

<Nucleic Acid Microarray>

The nucleic acid microarray as used herein means an array in which a probe nucleic acid is bonded, immobilized and onto the surface of a solid material (the surface as used herein is also called three-dimensional surface and surfaces of fibers and the like are also included therein, that is, in the case of a large shape, it is called a surface herein when it is substantially a surface even when it appears to be included). The solid material is not particularly limited, with the proviso that it is a material to which a probe nucleic acid can be bonded, such as a generally used slide glass or the like glass material, as well as a plastic material, a carbon fiber, a gel or sol, a membrane, a metal and the like. Shape of the solid material, such as plane, peak of a projection, granular, inside of a capillary or the like is not particularly limited too. A DNA microarray produced using a spotter and a DNA chip produced by a semiconductor technique are also included in the nucleic acid microarray of the invention.

According to the invention, a BAC-DNA array, an oligonucleotide microarray, a c-DNA microarray and the like can be used as the nucleic acid microarray. In addition, arrangement of spots of microarray is varied, and there are a multiple sample array which has two or more areas of array and can measure two or more samples to be tested on one basement, a tiling array which reproduced a large number of spots on one basement by combining two or more arrays, and the like.

There are various shapes of microarrays, and those in which the reaction efficiency was improved by forming a three-dimensional structure, those in which nucleic acid was bonded in a granular shape, those in which nucleic acid was bonded on a tape, and the like, as well as those in which nucleic acid was bonded in a CD or the like disc shape, can be cited.

The BAC-DNA array is not particularly limited and may be any array with the proviso that it is prepared based on a DNA under a state of introducing a mammalian or the like insert into BAC, including those to which itself is applied and those in which it is amplified using PCR or the like amplification technique.

<Probe Nucleic Acid>

The probe nucleic acid is a nucleic acid comprising a sequence in which its inclusion is known in advance, and in the case of a microarray, two or more of it is immobilized generally in the form of spots.

As the probe nucleic acid, a chemically synthesized nucleic acid, a cDNA, BAC (bacterial artificial chromosomes), YAC (yeast artificial chromosomes) and the like, and those in which these substances are amplified using genetic engineering techniques, can be used. Also, a nucleic acid prepared by chemically modifying a DNA, RNA or the like natural type nucleic acid may be used as a probe nucleic acid. For example, a PNA (peptide nucleic acid), a BNA (bridged nucleic acid), a methyl phosphonate type DNA, a phosphorothioate type DNA, a phosphoroamidate type DNA, a boranophosphate type DNA and the like can be used. In addition, a chimeric nucleic acid can also be used. For example, those in which a DNA moiety and an RNA moiety are mixed in a nucleic acid and a natural type nucleic acid and a modified type nucleic acid are mixed therein can be used.

Regarding the method for mounting a probe nucleic acid on a solid substrate, a method in which nucleotides are chemically synthesized one by one using an amidite monomer to which a photodesorption group typified by GeneChip is bonded and using a mask, a method in which a desired sequence is chemically synthesized by spotting an amidite monomer on a solid substrate by an ink jet method, a method in which a nucleic acid is synthesized on a substrate by changing pH of a solution on an electrode and releasing a protecting group making use of the change in pH, a method in which a nucleic acid chemically synthesized in advance is purified and spotted on a substrate, a method in which a cDNA is spotted using a spotter, and the like can be used. Regarding the spotting method, an ink jet method, a pin array method and the like can be used.

It is desirable that size of the probe nucleic acid is from 10 b to 10 kb, preferably from 50 b to 5 kb, more preferably from 100 b to 2 kb.

Spot

In general, a nucleic acid microarray has two or more of a region (spot) in which a probe nucleic acid having a substantially identical sequence is immobilized in a large amount and at high density, and the number of spots of the substantially the same species and the same amount of the probe nucleic acid which can be used in the invention may be one or more, independent of the number of spots. It can be optionally selected in response to the purpose of analysis.

Immobilizing amount of the probe nucleic acid is preferably from 0.8 to 5 µg, more preferably from 1.0 to 2.0 µg, per one spot.

The spot shape is not restricted, but a round shape is preferably used.

The diameter of the spot is not restricted, but 10 µM to 1000 µm is preferred.

<Sample to be Tested>

The sample to be tested according to the invention is a nucleic acid considered to be analyzed using a nucleic acid microarray (sample nucleic acid), a cell containing the nucleic acid, or the like, means all of those which are considered to be analyzed using a nucleic acid microarray, and is not particularly limited.

For example, it is an analyzing object which contains a nucleic acid to be used for the measurement of the expressed amount and presenting amount of a nucleic acid, the number of copies in genome, and the like, a cell to be used for the evaluation of diagnosis, or the like, but it also includes an organ, an individual and the like, so that it does not limited to a cell itself.

As other substances which can be considered as samples to be tested, those which are used in testing the ability of arrays and measuring instruments, and the like, using a substance in which the existing amount of a synthetic nucleic acid and the like are known or not known in advance, can also be considered as samples to be tested, and it is also possible to consider the verification nucleic acid which described later as a sample to be tested when it is regarded as an object of measurement.

As the sample to be tested, a nucleic acid which can be obtained from a patient or animal having a certain disease, a cell from which a nucleic acid can be obtained, and the like can be cited, and all of those which include cells are included. In a narrow sense, it means a nucleic acid. For example, as the disease, all of the diseases considered to have a possibility of having certain information on nucleic acids, such as a cancer, a hereditary disease, an inflammation and the like, come under the case, without other particular limitations.

In addition, a cancer sample to be tested to which an LCM (laser capture microdissection) treatment was applied can also be used.

The standard means all cases which include the above-mentioned nucleic acid having a certain degree of information in advance for comparing with a sample to be tested, a cell from which a nucleic acid can be obtained and details thereof. Even when different from a general existing amount, it is possible to regard it as a standard with the proviso that information can be obtained by comparing with a sample to be tested. For example, assuming that a cancer was generated in a patient having CNV or certain mosaic, and when a nucleic acid obtained from the cancer cell was compared with a cell obtained from a normal cell other than the cancer cell, it is considered that the CNV and certain mosaic are mutually eliminated so that there is no hindrance in using it as a standard.

In addition, even in the case of a nucleic acid prepared from a cell or the like having completely different origin, it is possible to regard it as a standard with the proviso that it can be used as a comparing object.

According to the invention, both of a sample nucleic acid extracted as a sample nucleic acid from a sample to be tested and a standard can be used, but as described in the foregoing, it is desirable to hybridize the sample nucleic acid extracted from a sample to be tested and the standard with separate arrays.

According to the invention, it is desirable to use a cancer cell-derived nucleic acid or a nucleic acid derived from a normal cell (a cell not causing cancer) as the sample nucleic acid.

Purification of Nucleic Acid

According to the invention, it is desirable to carry out purification in preparing a nucleic acid from a sample to be tested or a standard. In carrying out labeling, various side reactions are generated and proteins, lipids, saccharides and the like in cell lysate exert influence on the labeling reaction and exert a serious influence on the background noise, so that measuring capacity of a nucleic acid microarray is considerably lowered when purification is not carried out.

As the purification step, a method which uses a cartridge that carries a nucleic acid adsorbent membrane of silica, a cellulose derivative or the like, ethanol precipitation or isopropanol precipitation, phenol-chloroform extraction and the like can be used. Also useful are a method by a solid phase extraction cartridge which uses an ion exchange resin, a silica carrier to which octadecyl group or the like hydrophobic substituent group is linked, a resin having a size excluding effect or the like, and a method by a chromatography or the like. Among these, purification by a QuickGene Series (mfd. by Fuji Photo Film) in which a nucleic acid adsorbent porous membrane prepared by saponificating cellulose triacetate is kept in a cartridge is desirable. This is because a nucleic acid can be prepared semi-automatically using a low price machine, by the use of the QuickGene Series. In addition, this is very thin in comparison with the silica system nucleic acid adsorbent porous membrane and is suited for nucleic acid extraction with a small amount, so that a nucleic acid having markedly high concentration can be obtained in comparison with other methods. Also, this is a method suited for obtaining a labeled nucleic acid in a small amount and with a high concentration, because a nucleic acid having further high purity can be obtained in comparison with the ethanol precipitation method and isopropanol precipitation method which can perform purification with a small liquid volume. In addition, since a bad influence is exerted on the subsequent steps when the phenol-chloroform extraction method or other various precipitation methods are used, when a nucleic acid is prepared from a sample to be tested, two or more purification steps can also be carried out for the improvement of purity.

When purification from a sample to be tested is carried out by a column method in which a nucleic acid adsorbent membrane containing silica as the main component is immobilized to a cartridge and its recovered liquid volume is large in general, and concentration of the obtained nucleic acid becomes very thin. In order to solve this problem, it is possible to remove all of the solution by ethanol precipitation or the like or to concentrate it using an ultrafiltration column or the like.

According to the invention, it is more desirable to not carry out fragmentation of chain length of the nucleic acid extracted from a sample to be tested, from the viewpoint that the step is simple and the treating period of time is short, but fragmentation of the chain length of nucleic acid extracted from the sample to be tested, namely its shortening, can be effected by carrying out an enzyme treatment, an ultrasonic treatment, a mechanical fragmentation treatment, a chemical treatment or the like. In addition, the purification step can be carried out or the purification step can be omitted after carrying out these treatments.

In addition, when the purification step is carried out, according to the invention, purity of a nucleic acid is increased by fragmenting it with a restriction enzyme or the like nuclease and purifying the obtained nucleic acid, and also, a nucleic acid having further high purity and high concentration can be obtained by incorporating a concentration step at the time of purification, for example by extracting it with a recovering liquid volume smaller than the solution volume of the nucleic acid, so that it can be suitably used because the efficiency for obtaining a target nucleic acid becomes good.

As the enzyme to be used in the enzyme treatment, it is desirable to use a restriction enzyme or a nuclease. It is possible also to use two or more species of restriction enzymes.

The mechanical fragmentation treatment according to the invention means to carry out a reciprocal movement of a container toward a certain direction (however, an eight figure and the like movements are included). When balls such as of glass, stainless steel, zirconia or the like are added in carrying out this treatment, the treatment further advances and the nucleic acid is further digested, so that these can be suitably used. In addition, cutting by an ultrasonic treatment can also be carried out.

Subtraction Method

The method of the invention can also increase accuracy of the nucleic acid microarray measurement by a subtraction method. The subtraction method is a method for efficiently isolating a gene by subtracting, when there is a difference in the number of copies or expression of the gene of interest, the difference presenting in the gene by the knack of carrying out subtraction. For example, a PCR-Select method, an RDA (representation difference analysis) method, a DsDD (Duplex-specific Direct Digestion) method and the like can be used.

Particularly, in the case of a cancer cell, a large number of normal cells are contained in a cancer tissue together with the cancer cells, and as a result, performance of the nucleic acid microarray is considerably lowered in the case of the cancer cell, but the performance lowering can be prevented to a certain degree by the subtraction method.

<Labeling>

The labeling is an action to allow a detectable substance to bind to a nucleic acid, and so far as it is detectable, any substance can be incorporated into the invention. For example, a fluorescent material, an inorganic compound, an enzyme, a radioisotope, a pigment and the like can be included, and it is desirable that the labeling is effected by fluorescence. It is also possible to label two or more substances for one sample to be tested.

Fluorescent Material

As the fluorescent material, though its use is not particularly limited, all of fluorescein isothiocyanate (FITC), Cy-dye, ALEXA, green fluorescent protein (GFP), blue fluorescent protein (BFP), yellow fluorescent protein (YFP), red fluorescent protein (RFP), acridine, DAPI, ethidium bromide, SYBR Green, Texas Red, a rare metal fluorescence labeling agent, TAMRA, ROX and the like substances can be used, with the proviso that they are commercially available or can be prepared, and preferably, fluorescence labeling can be made by cy-3 or cy-5.

As the inorganic compound, though its raw material to be used is not particularly limited, for example, a quantum dot made of a semiconductor inorganic material can be cited. As its example, nanoparticulate of silica, CdTe, ZnSe or CdSe can be cited. This particulate can change its generating fluorescence wavelength by changing its particle diameter, and it becomes blue at a diameter of 2 nm, green at a diameter of 3 nm, yellow at a diameter of 4 nm and red at a diameter of 5 nm. Accordingly, its fluorescence may be detected, or the presence of its particle may be directly detected. For example, as a means for directly detecting the presence of particle, an AFM (atomic force microscope) or an electron microscope can be used.

Further, digoxigenin (DIG), biotin and the like can also be used. As an example of the application of biotin, it can be used in the detection of purple color development which can be seen when avidin is allowed to bind to biotin that has been linked to a probe, biotin-linked alkaline phosphatase is allowed to bind thereto, and then nitro-blue tetrazolium and 5-bromo-4-chloro-3-indolyl phosphate are added thereto as substrates of the alkaline phosphatase.

In addition, it can be labeled non-enzymatically. For example, ULS arrayCGH Labeling Kit (mfd. by Kreatech Biotechnology BV) and the like can also be used.

Direct Labeling Method and Indirect Labeling Method

As the labeling method, either a direct labeling method or an indirect labeling method may be used in the invention. The direct labeling method is a method in which, when Cy-dye is used for example, a nucleic acid is converted into single strand, a short chain nucleic acid is allowed to hybridize therewith and a Cy-dye-linked nucleotide derivative is mixed therewith together with nucleotides, all in advance, and then a labeled nucleic acid is synthesized at one step. Though there is a problem in that the uptake efficiency when an enzyme uptakes a non-natural type nucleotide derivative is lower than that of a natural type nucleotide, the step is convenient and it can be suitably used in the invention. The indirect labeling method is a method in which, when Cy-dye is used for example, a nucleic acid is converted into single strand, a short chain nucleic acid is allowed to hybridize therewith and a nucleotide derivative having a substituent group to which Cy-dye can be linked, such as a nucleotide derivative having aminoallyl group, is mixed therewith together with natural type nucleotides, all in advance, and a labeled nucleic acid is obtained by firstly synthesizing a nucleic acid having this substituent group and then allowing Cy-dye to linked thereto via aminoallyl group. Though the process of this method is complex, three-dimensional structure of the nucleotide derivative to which aminoallyl group was bonded is structurally closer to the natural type nucleotide than the Cy-dye-bonded nucleotide derivative to be used in the direct labeling method and its efficiency to uptake a labeling compound is high, so that this can also be suitably used in the invention.

According to the invention, a random primer method (primer extension method), a nick translation method, a PCR (polymerase chain reaction) method, a terminal labeling method and the like can be used as the method for introducing a labeling compound into a nucleic acid. The random primer method can be suitably used particularly in the invention.

The random primer method is a method in which a random primer nucleic acid of from several by (base pair) to a little over ten by is allowed to hybridize with a nucleic acid and a labeled nucleic acid is synthesized by simultaneously carrying out amplification and labeling using a polymerase. The nick translation method is a method in which a DNA is degraded by allowing a DNA polymerase to act upon a double-stranded nucleic acid nicked, for example, with DNase I, and a labeled nucleic acid is synthesized at the same time by the DNA polymerase activity. The PCR method is a method in which a labeled nucleic acid is obtained by preparing two species of primer and by simultaneously carrying out amplification and labeling through a PCR reaction using the primers. The terminal labeling method is, in the case of labeling the 5' end, a method in which a labeling compound is incorporated into the 5' end of a nucleic acid dephosphorylated with alkaline phosphatase, effected by the phosphorylation reaction of T4 polynucleotide kinase. The method for labeling 3' end is a method in which a labeling compound is added to the 3' end of a nucleic acid by a terminal transferase.

Dye Swapping Method

A dye swapping method can also be used in the invention. In the dye swapping method as described herein, for example, samples in which a nucleic acid derived from a standard cell is labeled with Cy3, and a verification nucleic acid with Cy5, are allowed to hybridize on a first nucleic acid microarray, and samples in which a nucleic acid derived from a sample cell is labeled with Cy3, and a verification nucleic acid with Cy5, are allowed to hybridize on a second nucleic acid microarray. A ratio is calculated from the fluorescence values obtained from the first and second nucleic acid microarrays. Next, samples in which a nucleic acid derived from a standard cell is labeled with Cy5, and a verification nucleic acid with Cy3, are allowed to hybridize on a third nucleic acid microarray, and samples in which a nucleic acid derived from a sample cell is labeled with Cy5, and a verification nucleic acid with Cy3, are allowed to hybridize on a fourth nucleic acid microarray. A ratio is calculated from the fluorescence values obtained from the third and fourth nucleic acid microarrays. This is a method in which a difference in enzyme incorporation efficiency due to labeling compounds is corrected by such a method.

Deactivation of Enzyme Activity

According to the invention, as the labeled sample nucleic acid and labeled verification nucleic acid, it is also possible to use un-purified solutions containing them. When such un-purified solutions are used, an enzyme and the like are remained a such in these solutions, so that it is desirable to deactivate activity of the enzyme remaining in the solutions, after their preparation. This is because, for example, in the case of labeling a labeled sample nucleic acid derived from a sample to be tested with Cy3, and a labeled verification nucleic acid with Cy5, there is a step for mixing un-purified solutions containing them, and when the remaining enzyme is present in the solutions at the time of this mixing, there is a possibility that the labeled sample nucleic acid is further labeled with Cy5, and the labeled verification nucleic acid with Cy3, by the remained enzyme, thus posing a possibility that it exerts influence on the reproducibility of data.

According to the invention, any method which can deactivate enzymes may be used as the enzyme deactivation method, but it is desirable to carry out either one or both of a method for adding a chelating agent and a heat treatment at 60° C. or more. The heating temperature is preferably 60° C. or more, more preferably 63° C. or more. The heating period of time may be 1 minute or more, but most desirably, it is desirable to carry out a heating treatment at 65° C. or more for 5 minutes or more.

In addition, in the case of a labeling method which uses Klenow fragment, it is possible to deactivate activity of the enzyme using a Vortex mixer or the like.

Labeled Nucleic Acid

The labeled nucleic acid means a nucleic acid to which a labeling compound is bonded, and it may be purified or not purified.

Purified Solution Containing Labeled Nucleic Acid

The purified solution containing labeled nucleic acid means a nucleic acid solution obtained by applying a purification step to a solution containing a labeled nucleic acid. In this case, the purification step is a step for removing unreacted labeling compound, enzyme and the like after carrying out the labeling treatment, but since it also includes a means for removing nucleic acids which do not contribute to the hybridization and bio-materials and chemical materials which exert influence on the subsequent hybridization, any occasion in which certain materials are removed before or after the step is regarded as the purification step.

Un-Purified Solution Containing Labeled Nucleic Acid

The un-purified solution containing labeled nucleic acid means a nucleic acid solution obtained by not carrying out a purification step after carrying out the labeling step on the solution of nucleic acid extracted from a sample to be tested. In this case, the purification step is a step for removing unreacted labeling compound, enzyme and the like after carrying out the labeling treatment, but a purification step for preparing a nucleic acid solution is not included therein. Since purification is not carried out, this is a nucleic acid solution, coexisting with various unreacted compounds added by the labeling step, such as primers, enzymes, nucleotides, ions contained in the buffer, and the like. In addition, a nucleic acid solution after carrying out heating, addition of a chelating agent or the like treatment on the un-purified solution containing labeled nucleic acid, with the aim of deactivating the coexisting enzyme, is also called un-purified solution containing labeled nucleic acid in the invention.

<Verification Nucleic Acid>

The verification nucleic acid is a nucleic acid which, on all of the spots of object, has a sequence capable of hybridizing at least a part of the probe nucleic acid, can detect abnormality of hybridizing ability in the spot of interest, illustratively an abnormality caused by the amount of the probe nucleic acid immobilized onto said spot, and is further used for correcting spotting amounts of the probe nucleic acid between abnormal spots. Thus, the verification nucleic acid may be any nucleic acid which can hybridize with the probe nucleic acid immobilized to all spots on the nucleic acid microarray, and may have any sequence or chain length. In this case, the all spots represent all of the spots having a possibility of reacting with the sample to be tested and standard in the same solution and are generally all spots on a single nucleic acid microarray.

In addition, it may be any nucleic acid so far as it can perform hybridization, and a DNA, RNA or the like wild type nucleic acid or a nucleic acid prepared by chemically modifying the DNA, RNA or the like wild type nucleic acid may be used. For example, a PNA (peptide nucleic acid), a BNA (bridged nucleic acid), a methyl phosphonate type DNA, a phosphorothioate type DNA, a phosphoroamidate type DNA, a boranophosphate type DNA and the like can be used. Also, a chimeric nucleic acid can also be used. For example, those in which a DNA moiety and an RNA moiety are mixed in a nucleic acid and a natural type nucleic acid and a modified type nucleic acid are mixed therein can be used.

As the labeled verification nucleic acid (B), for example, a nucleic acid sequence considered to be present in the all spots when an array is prepared, such as a repeated sequence, a vector, *Escherichia coli* genome or the like, can be used, and it is desirable to use a nucleic acid which is different from the sample to be tested and has a sequence on the first and $n^{th}$ probe nucleic acids.

As the vector, a plasmid, a BAC, a YAC, a PAC, a cosmid, a virus and the like various vectors can be cited, and any vector used in preparing an array or a nucleic acid having the same sequence with this vector may be used.

A repeated sequence can be cited as a sequence which is desirable as the verification nucleic acid. The repeated sequence is also called a repetitive sequence, which is a restriction enzyme recognition region or the like sequence that repeatedly appears every certain number of bases, its examples include a sequence which repeats a pattern of short nucleotide sequence many times, such as poly d(AT), poly d(GC) or the like, and a sequence in which a long sequence of reaching several thousand base pairs per one unit is repeated many times, and it is known that this appears at a high frequency in the genome of human and the like higher life. According to the invention, for example, the Cot-1 DNA available from Invitrogen can be suitably used.

For example, it is desirable to use the Cot-1 DNA in the case of a nucleic acid microarray which uses a mammalian BAC-DNA. The Cot-1 DNA is a nucleic acid which is generally used for blocking a repeated sequence in a sample to be tested obtained from mammalian at the time of nucleic acid microarray measurement, and in the case of a nucleic acid microarray which uses a mammalian BAC probe, generally in the prove, a repeated sequence is contained in substantially many BAC probes.

For example, in the case of a nucleic acid microarray which uses a BAC-DNA having a repeated sequence in the probe, by blocking the repeated sequence presenting on the target nucleic acid and probe nucleic acid through nonspecific hybridization by adding the Cot-1 DNA, nonspecific hybridization of the repeated sequence presenting on the target nucleic acid side with the probe nucleic acid presenting on the probe nucleic acid side is prevented, so that the fluorescence value originated from the specific hybridization can be selectively detected. According to the invention, it was found that it is possible to increase detection sensitivity of specific hybridization and to reduce a difference between spots, using the Cot-1 DNA by labeling at least a portion thereof (preferably together with an un-labeled nucleic acid identical to the same species (i.e. having the same sequence) of the labeled verification nucleic acid, for example un-labeled Cot-1 DNA).

In addition, a synthetic oligonucleotide having a nucleic acid sequence substantially complementary to a nucleic acid sequence moiety which is commonly present in probe nucleic acids can also be used as the verification nucleic acid.

According to the invention, it is desirable to use the verification nucleic acid in an amount of 1 or more in molar ratio based on nucleic acids. This is because capacity of the nucleic acid microarray is improved by the use of q or more of molar ratio.

Size of the verification nucleic acid is preferably 20 bp or more, more preferably from 20 bp to 1 Mbp, further preferably from 100 bp to 500 kb.

It is desirable that using amount of the verification nucleic acid is set to a range of from 0.5 to 2 times moles based on the nucleic acid of the sample to be tested or of the standard.

Labeled Verification Nucleic Acid (B)

The labeled verification nucleic acid (B) means a verification nucleic acid in which a labeling compound is linked to the verification nucleic acid, and it is called labeled verification nucleic acid in the invention when it is purified or not purified.

As the labeled verification nucleic acid, a nucleic acid derived from a sample to be tested, a nucleic acid derived from a normal cell or a nucleic acid containing a repeated sequence can be used, and it is desirable to use Cot-1 DNA.

It is desirable to use the labeled verification nucleic acid in an amount of 1 mole or more, more desirable to use it in an amount of 3 moles or more, most desirably 8 moles or more, based on the sample nucleic acid (A).

Purified Solution Containing Labeled Verification Nucleic Acid

The purified solution containing labeled verification nucleic acid means a solution containing labeled verification nucleic acid, obtained by applying a purification step to a solution containing the labeled verification nucleic acid (B). In this case, the purification step is a step for removing unreacted labeling compound, enzyme and the like after carrying out the labeling treatment.

Unpurified Solution Containing Labeled Verification Nucleic Acid

The unpurified solution containing labeled verification nucleic acid means a solution containing a labeled verification nucleic acid, obtained by not carrying out a purification step on the solution containing the labeled verification nucleic acid (B). Since purification is not carried out, this is a solution containing a labeled verification nucleic acid, in which various unreacted compounds added by the labeling step, such as primers, enzymes, nucleotides, ions contained in the buffer, and the like are coexisted. In addition, a nucleic acid solution after carrying out heating, addition of a chelating agent or the like treatment on the unpurified solution containing labeled verification nucleic acid, with the aim of deactivating the remaining enzyme, is also called unpurified solution containing labeled verification nucleic acid in the invention.

<Blocking Agent>

The blocking agent as described herein is used for reducing detection of nonspecific hybridization at the time of the hybridization, and can be added together with the labeled sample nucleic acid (A), labeled verification nucleic acid (B) and the like at the time of preparing a hybridization solution. For example, it means tRNA (transfer RNA), denatured salmon sperm DNA, poly A, poly dA, skim milk and the like substances which mainly have a function to reduce background noise of nucleic acid microarray, and a blocking agent which is generally on the market can also be used.

<Composition of Hybridization Solution>

The invention can use the following substances as a composition of the hybridization solution. For example, in the case of a nucleic acid microarray which uses a BAC-DNA, dextran sulfate having an action to increase nucleic acid concentration and a function to keep an area to a certain degree even when partitioned by increasing viscosity, formamide having an action to lower melting point of nucleic acid and solution which can increase ionic strength and has a function to keep pH at a constant level can be cited as examples.

According to the invention, it is desirable to use a solution containing the following reagents.

Polyethylene glycol (PEG, JP-A-2000-325099), dextran sulfate or the like can be used as a substance having excluded volume effect.

Formamide, glycerol, formaldehyde, DMSO, DMF, GuSCN, iodine or the like can be used as a compound which lowers melting point.

In addition to SSC, SSPE can be generally cited as a solution for adjusting ionic strength. Other than these, MES hybridization buffer and the like can be used.

<Hybridization Solution>

The hybridization solution as described in the invention is a solution in which the above-mentioned reagent and blocking agent and other reagent, labeled sample nucleic acid and verification nucleic acid are mixed, is a solution which has a property to optimize hybridization of the labeled sample nucleic acid (A) and labeled verification nucleic acid (B) with a probe nucleic acid on the nucleic acid microarray, and is a solution which accelerates a hybridization having high consistency of sequences between the probe nucleic acid and the labeled sample nucleic acid and labeled verification nucleic acid, and on the other hand, has an action to inhibit a hybridization having low consistency of sequences.

In addition to these, as described in JP-A-2005-087109, a phospholipid, a Denhardt solution (a solution containing Ficoll, polyvinyl pyrrolidone and bovine serum albumin as the main components), a quaternary ammonium salt, betaine (Biochemistry, 32, 137-144 (1993)), TMAC (tetramethyl ammonium chloride) (Proc. Natl. Acad. Sci. USA, 82, 1585-1588 (1985)), a commercially available hybridization solution, such as ExpressHyb (Clontech), PerfectHyb (TOYOBO), ULTRAhyb (Ambion or the like), or the like can be used in the invention as one of the composition of the hybridization solution.

A surfactant can also be added to the hybridization solution. As the surfactant, a cationic surfactant, an anionic surfactant or a nonionic surfactant can also be used. As the anionic surfactant, it is desirable to use sodium dodecyl sulfate. Sodium dodecyl sulfate can efficiently suppress background. In addition to this, N-lauryl sarcoside, lithium lauryl sulfate and the like are used. As the nonionic surfactant, Tween (registered trademark), Triton X (registered trademark) and the like are known. These surfactants can be used in the invention.

Hybridization Solution Containing Labeled Sample Nucleic Acid (A) and Labeled Verification Nucleic Acid (B)

The hybridization solution containing labeled sample nucleic acid and labeled verification nucleic acid as described in the invention means a hybridization solution into which at least one species of labeled sample nucleic acid and at least one species of labeled verification nucleic acid are entrapped.

Hybridization Solution Containing Labeled Sample Nucleic Acid (A), Labeled Verification Nucleic Acid (B) and Blocking Agent The hybridization solution containing labeled sample nucleic acid, labeled verification nucleic acid and blocking agent as described in the invention means a hybridization solution into which at least one species of labeled sample nucleic acid, at least one species of labeled verification nucleic acid and at least one species of blocking agent are entrapped.

Preparation of Hybridization Solution Containing Various Nucleic Acids

Preparation of a Hybridization Solution which does not Contain a Labeled sample nucleic acid but contains other nucleic acids may be carried out by the user, but it may be prepared and provided by a provider of arrays and the like. When the labeled verification nucleic acid (B) is contained in this hybridization solution, it is desirable to unify concentration and kind of the labeled verification nucleic acid, batch number of the product, and the like, so that the user can easily carry out a nucleic acid microarray test having high accuracy.

That is, it is desirable also to concentrate or purify at least either one of the labeled sample nucleic acid (A) prepared in the above-mentioned step (a) and the labeled verification nucleic acid prepared in the step (b), and it is desirable also to concentrate or purify the hybridization solution prepare in the step (c).

Concentration

When concentration of the hybridization solution which does not contain a labeled sample nucleic acid but contains other nucleic acids is carried out in advance, it becomes possible to carry out a nucleic acid microarray having high accuracy. That is, it is considered that a test having further high accuracy can be carried out because the frequency of meeting the hybridizing nucleic acids with each other becomes high.

Purification

The term "purification" as described in the invention is used synonymously with extraction, separation and fractionation.

In addition, as a means for this, a method which uses a cartridge that carries a nucleic acid adsorbent membrane of silica, a cellulose derivative or the like, ethanol precipitation or isopropanol precipitation, phenol-chloroform extraction, a solid phase extraction cartridge which uses an ion exchange resin, a silica carrier to which octadecyl group or the like hydrophobic substituent group is linked or a resin having a size excluding effect, and a method by a chromatography can be included therein.

<Method for Reading Off Hybridization>

The method for reading off hybridization on the nucleic acid array may be any method which can measure a label and is not limited.

For example, an X-ray film or BASS (Fuji Photo Film) can be used in the case of a radioisotope.

A method which uses a fluorescence scanner is the method most suitably used in the invention. This is suitably used when a fluorescent material is used as the labeling compound of labeled nucleic acids. As the fluorescence scanner, for example, an FLA series (Fuji Photo Film), a GenePix series (Axon Instruments), LS Reloaded (Tecan) and the like can be cited, though not particularly limited with the proviso that it is an apparatus which can read out microarray.

In addition, when a nucleic acid can be measured without labeling and a correction or the like calculation can be carried out, it cannot be said that labeling is an essential condition. For example, measurement by an SPR system can be considered.

<Automation>

Regarding the method of the invention, all steps can be carried out by manual labor, some steps can be carried out using automated machines or all steps can be carried out using automated machines. By carrying out automation, workers are released from troublesome works, labor cost is lowered, and a human error can be prevented by reducing a difference between results due to difference in the skillfulness.

<Provision of Data>

According to the invention, it is possible to employ a technique in which a special standard is measured in advance, and a sample to be tested is evaluated by providing the same. As a result of this, it becomes possible to carry out hybridization of samples to be tested alone without always preparing the standard, so that it becomes possible to carry out tests efficiently. In addition, it is also possible to use the data on samples to be tested by regarding them as the standard.

<Program>

When the data obtained by carrying out a nucleic acid microarray measurement are treated, in order to carry out it efficiently, it is possible to carry out a data processing which uses a program.

Said program is provided generally in the form of recording it on a computer-readable recording medium. Said recording medium is not particularly limited with the proviso that it can be read by a computer. Both of the transportable type and fixed type media are included in the recording medium of the invention, and for example, a compact disk (CD), a flexible disk (FD), a digital video disk (DVD), a hard disk, a semiconductor memory and the like can be cited.

The program of the invention can be circulated by recording it on the above-mentioned recording medium, or can be circulated in the form of recording it on the recording device of a computer in advance and transferring it to other computers through a network.

The kit for the analytical method of the invention contains a nucleic acid microarray having a plurality of spots onto each of which a probe nucleic acid is immobilized, and a verification nucleic acid that has a sequence capable of hybridizing with at least respective parts of the probe nucleic acids at all spots on the nucleic acid microarray. The verification nucleic acid may be preliminary labeled or may be labeled at the time of use by a user. Further, it is preferred that the verification nucleic acid is provided as a component for controlling ion strength or a hybridization solution containing a surfactant, etc.

EXAMPLES

The following describes the invention further in detail based on examples, but the invention is not limited thereto.

In this connection, unless otherwise noted, the term % represents % by mass.

Comparative Example 1

Nucleic Acid Microarray Test and Analysis, in the Case of Using an Unpurified Labeled Nucleic Acid as the Sample and Not Using a Verification Nucleic Acid <Preparation of Unpurified Labeled Nucleic Acid>

A 1.7 ml capacity micro tube (platinum tube, mfd. by BM Equipment) was charged with 3 µl (0.75 µg) of a female DNA G 1521, mfd. by Promega), 8 µl of water (distilled water, DNase- and RNase-free, mfd. by GIBCO) and 20 µl of 2.5× Random Primers Solution (mfd. by Invitrogen) of BioPrime (R) Array CGH Genomic Labeling System, and heat treatment was carried out at 95° C. for 5 minutes on BLOCK INCUBATOR BI-535A (mfd. by ASTEC). Five minutes thereafter, the micro tube was taken out to carry out 10 minutes of rapid cooling treatment on ice. A 5 µl portion of 10×dCTP Nucleotide Mix (mfd. by Invitrogen) of BioPrime (R) Array CGH Genomic Labeling System, 3 µl of 250 nmol Cy3-dCTP Bulk Pack (mfd. by GE Healthcare Bio-Science)

and 1 μl of Exo-Klenow Fragment (mfd. by Invitrogen) of BioPrime (R) Array CGH Genomic Labeling System were added thereto and amplification reaction and labeling reaction were carried out at 37° C. for 2 hours on the BLOCK INCUBATOR BI-535A. Two hours thereafter, the micro tube was taken out from the incubator and subjected to a heating treatment on the BLOCK INCUBATOR BI-535A which had been set to 65° C., thereby inactivating the Exo-Klenow Fragment contained in the reaction solution.

By carrying out the above-mentioned operation also on a male DNA, two species of un-purified nucleic acid were obtained. In this connection, the Cy3-dCTP (mfd. by GE Healthcare Bio-Science) was also used for the male DNA as the labeling compound.

<Preparation of a Solution Containing Cot-1 DNA (Solution A)>

A 65 μl portion of Cot-1 DNA (65 μg, mfd. by Invitrogen) was put into a 1.7 ml capacity micro tube and 6.5 μl of 3 M sodium acetate (pH 5.2) and 167 μl of ethanol cooled to −20° C. were added thereto and mixed therewith, and then the mixture was allowed to stand at −80° C. for 10 minutes. Thereafter, centrifugation was carried out at 4° C. and at 1,5000 rpm for 30 minutes using a centrifuge MX-300 manufactured by TOMY SEIKO. After the centrifugation, since the precipitate accumulated on the bottom of the centrifugation tube, the supernatant was discarded while taking care in not sucking the precipitate. Next, the remaining ethanol was removed by allowing the centrifugation tube to stand for 10 minutes while opening its cap. Ten minutes thereafter, 18 μl of 20% SDS was added thereto and allowed to stand for 30 minutes. After 30 minutes, 20 μl of a solution (prepared by mixing and dissolving 1 g of dextran sulfate (mfd. by SIGMA), 5 ml of formamide and 1 ml of 20×SSC and then adjusting the liquid volume to 7 ml by adding water) was added thereto and thoroughly mixed by stirring.

In this connection, it is desirable that this step is not carried out by a user, but a kit producer prepares in advance.

<Preparation of Hybridization Solution>

A 20 μl portion of the female unpurified labeled nucleic acid prepared in the <Preparation of unpurified labeled nucleic acid>, 20 μl of water added for coinciding it with the condition of Example 1 and 38 μl of the solution A were put into a 1.7 ml capacity micro tube, and sufficient stirring (Vortex) treatment was carried out. In addition, in the same manner, 20 μl of the male unpurified labeled nucleic acid prepared in the <Preparation of unpurified labeled nucleic acid>, 20 μl of water added for coinciding it with the condition of Example 1 and 38 μl of the solution A were put into a 1.7 ml capacity micro tube, and sufficient stirring (Vortex) treatment was carried out.

<Regarding Nucleic Acid Array>

After mass culturing of a commercially available BAC clone, a BAC DNA was obtained by carrying out its extraction and purification using an ion exchange column (Plasmid Midi Kit 100, Cat. No. 12145, mfd. by QIAGEN).

Thereafter, the BAC DNA was digested with four base-recognizing enzymes RsaI, DpnI and HaeIII, and then ligation was carried out by adding an adapter.

Next, by carrying out its amplification by PCR method using a primer having the same sequence of one oligonucleotide of the adapter, a probe DNA having a length of approximately from 1,000 to 3,000 bp was obtained.

The thus obtained probe DNA was spotted on a glass substrate using GENESHOT (mfd. by NGK INSULATORS, Nagoya).

By this, a nucleic acid microarray having a total of 1,600 spots, in which two for each of 800 probe DNA species prepared from the BAC clones were respectively spotted on the glass substrate, was obtained and used in the following tests.

<Pretreatment of Nucleic Acid Microarray>

About 200 ml of a blocking solution (mfd. by Matsunami Glass) was put into a glass container, the above-mentioned nucleic acid microarray was soaked therein, and the blocking reaction was carried out for 20 minutes using SLIDE WASHER SW-4 (mfd. by JUJI FIELD) while moving the slide glass up and down. After 20 minutes of the reaction, the nucleic acid microarray was taken off from the blocking solution and put into a container filled with 200 ml of water. This was washed for 3 minutes using the SLIDE WASHER and, 3 minutes thereafter, again put into a container filled with 200 ml of fresh water and washed using the SLIDE WASHER. Three minutes thereafter, this was put into a container filled with 200 ml of ethanol and again washed using the SLIDE WASHER. Three minutes thereafter, the nucleic acid microarray was taken off and its centrifugation was carried out using a table top centrifuge Spin Dryer mini 2350 (mfd. by TOMY SEIKO) to dry the nucleic acid microarray.

After the blocking, the nucleic acid microarray was soaked in boiling water for 2 minutes, subsequently soaked in 70% ethanol of −20° C. for 2 minutes, in 85% ethanol of −20° C. for 2 minutes and in 100% ethanol of −20° C. for 2 minutes, and then the nucleic acid microarray was dried by carrying out 1 minute of centrifugation using the spin drier.

<Hybridization>

Hybridization was carried out based on the protocol described in "A Guidebook for Practical Use of Array CGH Diagnosis—Chromosomal Fine Structure Aberrancy to be Known Beforehand (written in Japanese)" (Iyaku (Medicine and Drug) Journal). Specifically, heating treatment of each of the two sample solutions prepared in <Preparation of hybridization solution> was carried out at 75° C. for 16 minutes. Thereafter, pre-incubation was carried out at 42° C. for 30 minutes or more. Each of the solutions was added dropwise to one plate for each of nucleic acid microarray, and a gap cover glass (24×50 mm) (mfd. by Matsunami Glass) was put thereon in such a manner that bubbles are not formed.

These two nucleic acid microarrays were put into Tight Box No. 1 (mfd. by CHOPLA), and the tight box was put into a constant temperature oven (HYBRIDIZATION INCUBATOR, HB-80, mfd. by TAITEC) to carry out hybridization at 37° C. for 16 hours. In this case, in order to prevent drying of the nucleic acid microarrays, a paper towel (kimtowel) was put into the tight box and 4 ml of 50% formamide/2×SSC solution was added to the top thereof <Washing of Nucleic Acid Microarray>

After carrying out the hybridization, each of the nucleic acid microarrays was put into a SUMILON tube filled with 45 ml of a solution of 2×SSC and soaked therein until the cover glass was peeled off spontaneously from the nucleic acid microarray. Next, each nucleic acid microarray from which the cover glass came off was put into a 50 ml capacity SUMILON tube (mfd. by Sumitomo Bakelite) filled with 45 ml of 50% formamide/2×SSC (pH 7.0) solution which had been heated to 50° C. in advance. This was put into the HYBRIDIZATION INCUBATOR to carry out 15 minutes of washing at 50° C. by shaking the stage at a speed of 30 revolutions per minute. Next, each nucleic acid microarray was put into a SUMILON tube filled with 2×SSC/0.1% SDS (pH 7.0) solution which had been heated to 50° C. in advance. This was put into a constant temperature incubator to carry out 30 minutes of washing at 50° C. by shaking the stage at a speed of 30 revolutions per minute. Next, each nucleic acid microarray was put into a 50 ml capacity SUMILON tube filled with 45 ml of 2×SSC solution and 5 minutes of washing was carried out at room temperature by shaking the stage at a speed of 30 revolutions per minute. After the washing, each nucleic acid microarray was dried by carrying out 1 minute of centrifugation using Spin Dryer-Mini MODEL 2350.

<Data Uptake>

The thus washed two microarrays were subjected to scanning using GenePix 4000B (mfd. by Axon Instruments).

<Data Processing>

By regarding the unpurified labeled nucleic acid Cy3-Female-derived fluorescence value as FF, and its background noise as BF, the unpurified labeled nucleic acid Cy3-Male-derived fluorescence value as FM, and its background noise as BM, the Log Ratio was calculated using Log Ratio=$\log_2\{(FF-BF)/(FM-BM)\}$. In this case, the Log Ratio values were calculated on all spots.

In this connection, though the background noise value was subtracted in this comparative example, there is a case in which the subtraction is not necessary.

In addition, a result of subtracting a Log Ratio value of a portion which corresponds to the autosome from a Log Ratio value of a portion that corresponds to the X-chromosome was also calculated as a difference in Log Ratio.

Since female has two X-chromosomes and male has one X-chromosome, value of the difference in Log ratio is theoretically 1.0.

<Results>

Figure 2:
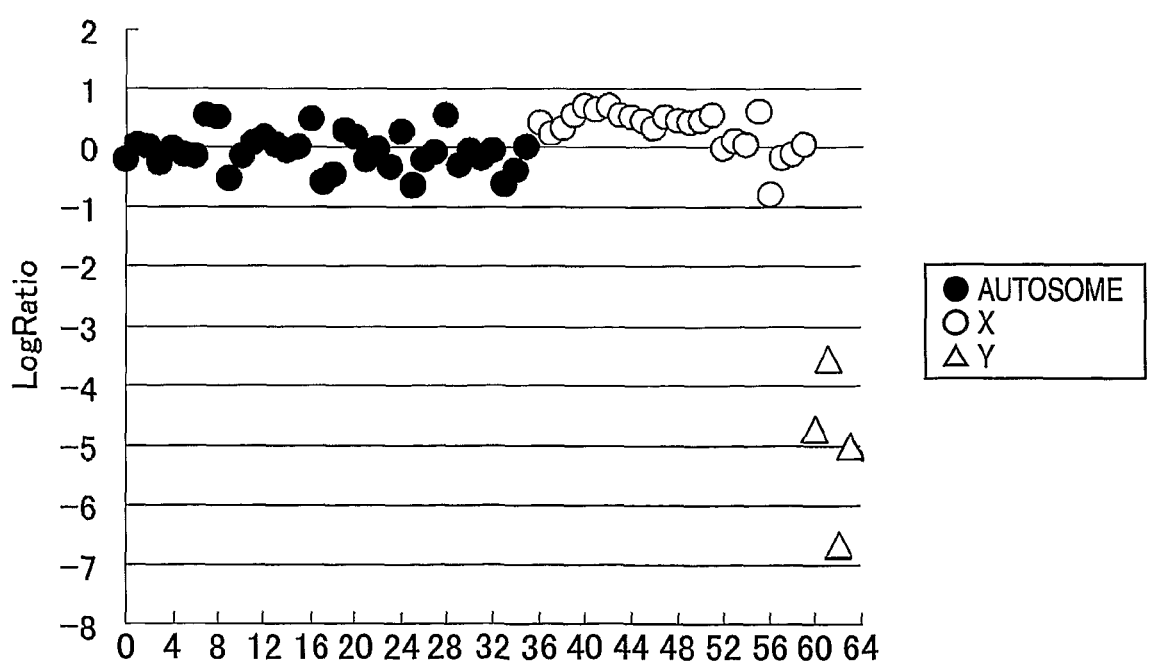
FIG. 2 is a result of carrying out comparison when a nucleic acid microarray was carried out using Female DNA as the sample to be tested and Male DNA as the standard, and not using a labeled verification nucleic acid.

A graph of the Log Ratio is shown in FIG. 2.

Inventive Example 1

Nucleic Acid Microarray Test and Analysis in the Case of Using Unpurified Labeled Nucleic Acid as the Sample and Unpurified Labeled Cot-1 DNA as the Verification Nucleic Acid <Preparation of Unpurified Labeled Nucleic Acid>

Respective unpurified labeled sample nucleic acids were prepared from a female-derived nucleic acid and a male-derived nucleic acid by the same method of the <Preparation of unpurified labeled nucleic acid> in Comparative Example 1.

<Preparation of Unpurified Labeled Verification Nucleic Acid>

A 1.7 ml capacity micro tube (platinum tube, mfd. by BM Equipment) was charged with 0.75 μg of Cot-1 DNA, 8 μl of water and 20 μl of 2.5×Random Primers Solution, and heat treatment was carried out at 95° C. for 5 minutes on the BLOCK INCUBATOR BI-535A. Five minutes thereafter, the micro tube was taken out to carry out 10 minutes of rapid cooling treatment on ice. A 5 μl portion of the 10×dCTP Nucleotide Mix, 3 μl of 250 nmol Cy5-dCTP Bulk Pack (mfd. by GE Healthcare Bio-Science) and 1 μl of the Exo-Klenow Fragment were added thereto, and an amplification reaction was carried out, together with a labeling reaction, at 37° C. for 2 hours on the BLOCK INCUBATOR BI-535A. Two hours thereafter, the micro tube was taken out from the incubator and subjected to a heating treatment on the BLOCK INCUBATOR BI-535A which had been set to 65° C., thereby effecting inactivation of the Exo-Klenow Fragment contained in the reaction solution.

<Preparation of Solution A>

Preparation of Solution a was Carried Out by the Same Method of Comparative Example 1.

<Preparation of Hybridization Solution>

A 20 μl portion of the unpurified labeled sample nucleic acid Cy3-Female prepared in the <Preparation of unpurified labeled nucleic acid>, 20 μl of the unpurified labeled verification nucleic acid Cy5-Cot-1 DNA prepared in the <Purification of unpurified labeled verification nucleic acid> and 38 μl of the solution A were put into a 1.7 ml capacity micro tube and sufficient stirring (Vortex) treatment was carried out. In addition, in the same manner, 20 μl of the unpurified labeled sample nucleic acid Cy3-Male prepared in the <Preparation of unpurified labeled nucleic acid>, 20 μl of the unpurified labeled verification nucleic acid Cy5-Cot-1 DNA prepared in the <Purification of unpurified labeled verification nucleic acid> and 38 μl of the solution A were put into a 1.7 ml capacity micro tube and sufficient stirring (Vortex) treatment was carried out.

<Pretreatment of Nucleic Acid Microarray>

This was carried out by the same method of the <Pretreatment of nucleic acid microarray> of Comparative Example 1.

<Hybridization>

Hybridization was carried out by the same method of the <Hybridization> of Comparative Example 1. In this case, a mixture of unpurified labeled sample nucleic acid Cy3-Female and unpurified labeled verification nucleic acid Cy5-Cot-1 DNA and a mixture of unpurified labeled sample nucleic acid Cy3-Male and unpurified labeled verification nucleic acid Cy5-Cot-1 DNA were respectively used as the sample.

<Washing of Nucleic Acid Microarray>

Washing of nucleic acid microarray was carried out by the same method of the <Washing of nucleic acid microarray> of Comparative Example 1.

<Data Uptake>

The thus washed two microarrays were subjected to scanning using GenePix 4000B (mfd. by Axon Instruments).

<Data Processing>

By regarding the unpurified labeled sample nucleic acid Cy3-Female-derived fluorescence value as FF, and its background noise as BF, fluorescence value of the unpurified labeled verification nucleic acid Cy5-Cot-1 DNA simultaneously hybridized with the unpurified labeled sample nucleic acid Cy3-Female as Fc1, its background noise as Bc1, the unpurified labeled sample nucleic acid Cy3-Male-derived fluorescence value as FM, its background noise as BM, fluorescence value of the unpurified labeled verification nucleic acid Cy5-Cot-1 DNA simultaneously hybridized with the unpurified labeled sample nucleic acid Cy3-Male as Fc2 and its background noise as Bc2, the fluorescence value FM' of the Male-derived unpurified labeled sample nucleic acid after correction was calculated by $$FM'=(Fc1-Bc1)/(Fc2-Bc2)\times(FM-BM).$$

The calculation was carried out on all spots. In this case, the fluorescence value FF' of the Female-derived unpurified labeled sample nucleic acid after correction may be calculated by the following formula.

$$FF'=(Fc2-Bc2)/(Fc1-Bc1)\times(FF-BF)$$

In this connection, though the background noise value was subtracted in this inventive example, there is a case in which the subtraction is not necessary.

In addition, the Log Ratio value was calculated by $$\text{Log Ratio}=\log_2\{(FF-BF)/FM'\}.$$

The calculation was carried out on all spots.

In this connection, when the FF' was calculated, the Log Ratio value can be calculated using $$\text{Log Ratio} = \text{Log}_2\{FF'/(FM-BM)\}.$$

Figure 3:
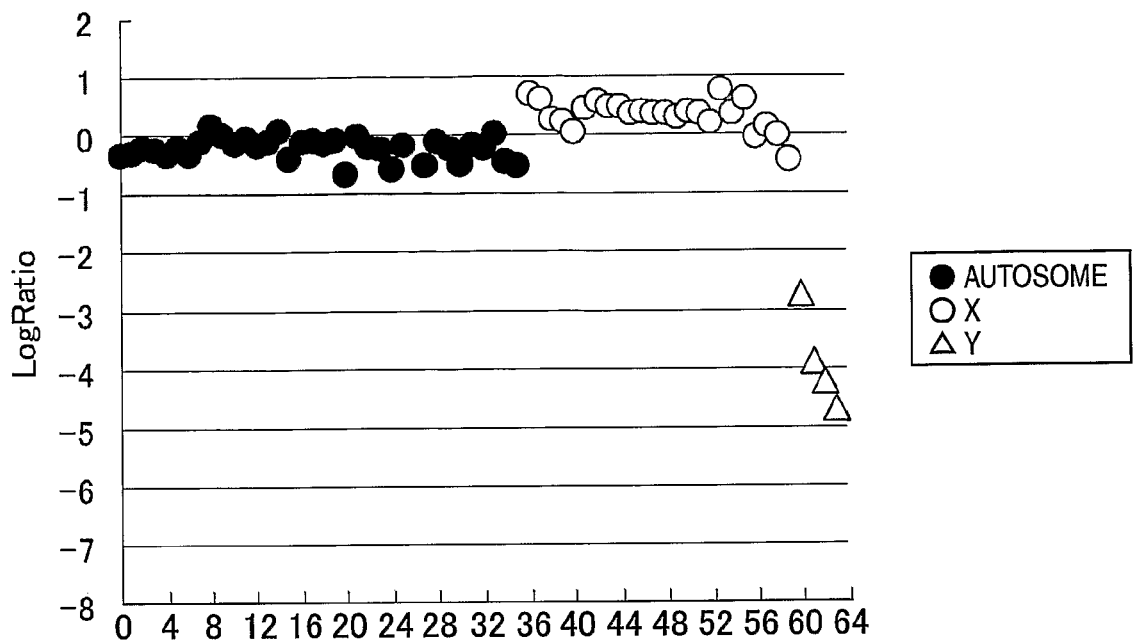
FIG. 3 is a result of carrying out comparison when a nucleic acid microarray was carried out using Female DNA as the sample to be tested and Male DNA as the standard, and the labeled quantity values were corrected using a labeled verification nucleic acid.

A difference in Log Ratio was obtained by calculating it in the same manner in Comparative Example 1.
<Results>
Plotting of the Log Ratio is shown in FIG. 3.

When FIG. 2 of Comparative Example 1 was compared with FIG. 3 of Inventive Example 1, plots of autosome were generally around zero point in the case of those in which correction by the unpurified labeled verification nucleic acid Cy5-Cot-1 DNA was carried out.

Figure 4:
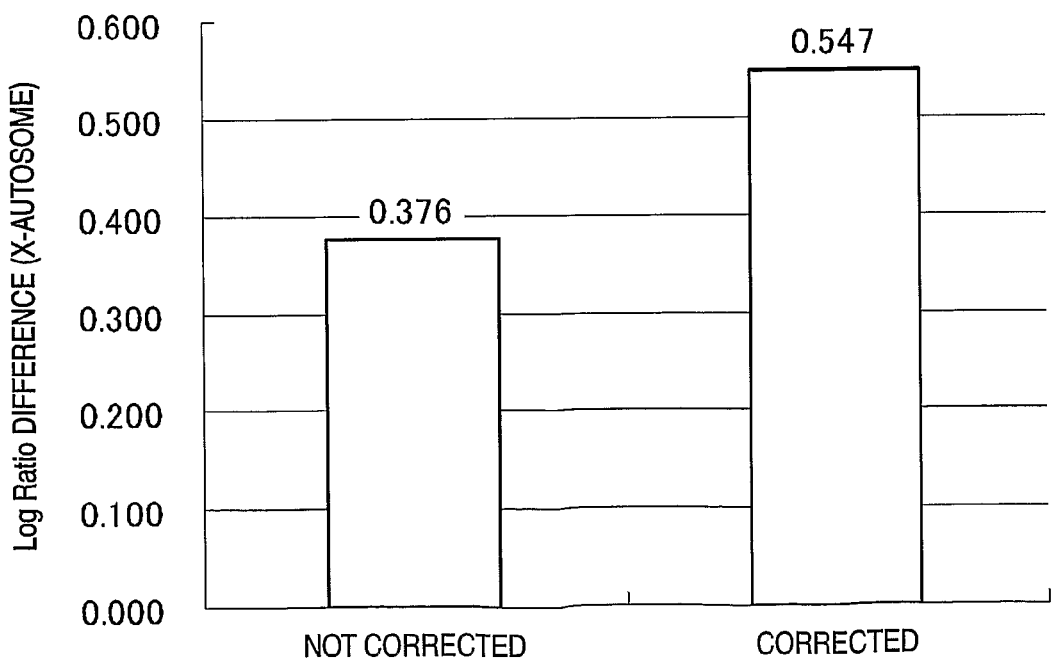
FIG. 4 shows a difference in Log Ratio between a case in which Female DNA was used as the sample to be tested and Male DNA as the standard, and correction was carried out using a labeled verification nucleic acid and a case in which the correction was not carried out by not using the labeled verification nucleic acid.

A drawing in which a difference in Log Ratio was plotted is shown in FIG. 4. In this connection, the difference in Log Ratio was obtained by the same method of Comparative Example 1. That is, the difference in Log Ratio was calculated from the difference between the average value of Log Ratio of X-chromosome moiety and the average value of Log Ratio of autosome moiety. Larger value of this difference means superiority as a nucleic acid microarray measurement. It became 0.38 when the correction was not carried out, and 0.55 when the correction was carried out, so that the difference in Log Ratio was increased by a factor of about 0.17 by carrying out the correction. To begin with, the number of X-chromosomes is different when male and female are compared so that there must be a difference from the case of autosome. When the difference is clearer, a change in the number of copies can be grasped with further high sensitivity, and more correct judgment can be made. That is, the fact that a difference in Log Ratio shows effectiveness of the use of a verification nucleic acid.

Figure 5:
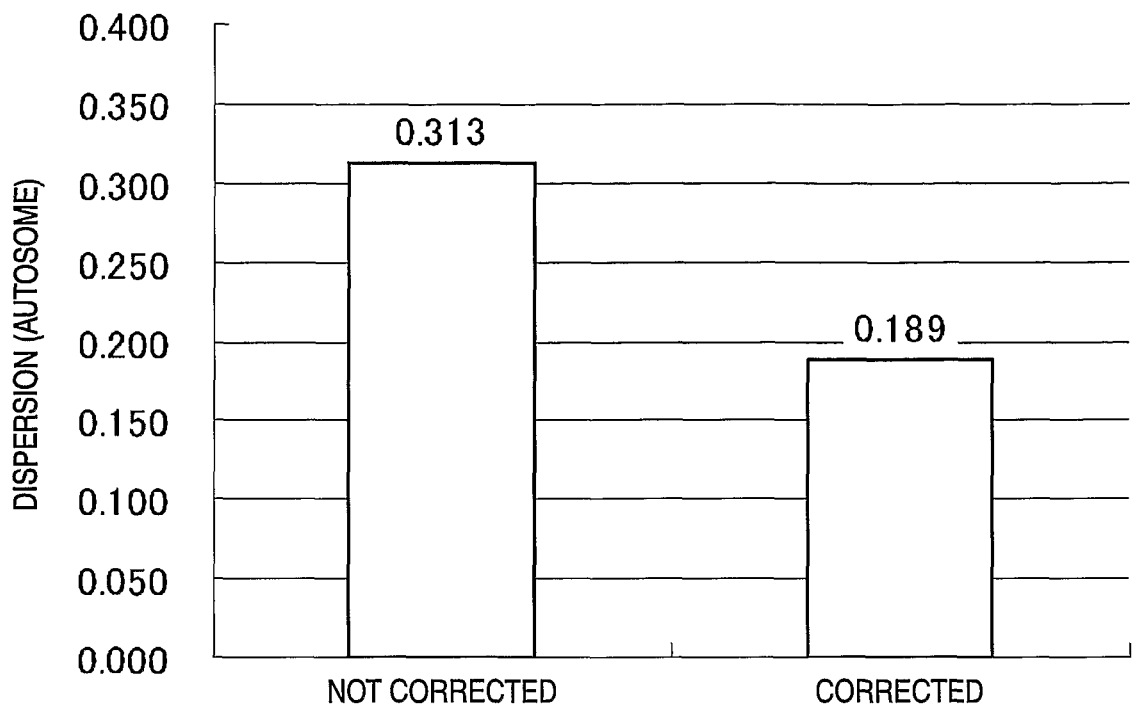
FIG. 5 shows a dispersion between a case in which Female DNA was used as the sample to be tested and Male DNA as the standard, and correction was carried out using a labeled verification nucleic acid and a case in which the correction was not carried out by not using the labeled verification nucleic acid.

FIG. 5 shows average values of dispersion calculated only on the autosomal moieties of parts which correspond to the female-derived and male-derived autosomal moieties. In the case of carrying out the correction, the dispersion becomes 0.189 which is a very small numerical value in comparison with the uncorrected dispersion of 0.313 and is close to the true value, thus showing the effectiveness of the use of a verification nucleic acid.

Inventive Example 2

Nucleic Acid Microarray Test and Analysis in the Case of Using Unpurified Labeled Nucleic Acid as the Sample and Unpurified Labeled Verification Nucleic Acid as the Verification Nucleic Acid <Preparation of Unpurified Labeled Nucleic Acid>
Respective unpurified labeled sample nucleic acids were prepared from a female-derived nucleic acid and a male-derived nucleic acid by the same method of Comparative Example 1.
<Preparation of Unpurified Labeled Verification Nucleic Acid>
A female-derived unpurified labeled nucleic acid was used as the unpurified labeled verification nucleic acid in this inventive example. In this case, Cy3 was used as the labeling compound.
<Preparation of Solution A>
Preparation of Solution a was Carried Out by the Same Method of Comparative Example 1.
<Preparation of Hybridization Solution>
A 20 μl portion of the unpurified labeled sample nucleic acid Cy5-Female prepared in the <Preparation of unpurified labeled nucleic acid>, 20 μl of the unpurified labeled verification nucleic acid Cy3-Female DNA prepared in the <Purification of unpurified labeled verification nucleic acid> and 38 μl of the solution A were put into a 1.7 ml capacity micro tube and sufficient stirring (Vortex) treatment was carried out.
In addition, in the same manner, 20 μl of the unpurified labeled sample nucleic acid Cy5-Male prepared in the <Preparation of unpurified labeled nucleic acid>, 20 μl of the unpurified labeled verification nucleic acid Cy3-Female DNA prepared in the <Purification of unpurified labeled verification nucleic acid> and 38 μl of the solution A were put into a 1.7 ml capacity micro tube and sufficient stirring (Vortex) treatment was carried out.
<Pretreatment of Nucleic Acid Microarray>
This was carried out by the same method of the <Pretreatment of nucleic acid microarray> of Comparative Example 1.
<Hybridization>
Hybridization was carried out by the same method of the <Hybridization> of Comparative Example 1. In this case, a mixture of unpurified labeled sample nucleic acid Cy5-Female and unpurified labeled verification nucleic acid Cy3-Female and a mixture of unpurified labeled sample nucleic acid Cy5-Male and unpurified labeled verification nucleic acid Cy3-Female were respectively used as the sample.
<Washing of Nucleic Acid Microarray>
This was carried out by the same method of the <Washing of nucleic acid microarray> of Comparative Example 1.
<Data Uptake>
The thus washed two microarrays were subjected to scanning using GenePix 4000B (mfd. by Axon Instruments).
<Data Processing>
By regarding the unpurified labeled sample nucleic acid Cy5-Female-derived fluorescence value as FF, and its background noise as BF, fluorescence value of the unpurified labeled verification nucleic acid Cy3-Female DNA simultaneously hybridized with the unpurified labeled sample nucleic acid Cy5-Female as Fc1, its background noise as Bc1, the unpurified labeled sample nucleic acid Cy5-Male-derived fluorescence value as FM, its background noise as BM, fluorescence value of the unpurified labeled verification nucleic acid Cy3-Female DNA simultaneously hybridized with the unpurified labeled sample nucleic acid Cy5-Male as Fc2 and its background noise as Bc2, the fluorescence value FM' of the Male-derived unpurified labeled sample nucleic acid after correction was calculated by $$FM' = (Fc1-Bc1)/(Fc2-Bc2) \times (FM-BM).$$

The calculation was carried out on all spots.

In this connection, though the background noise value was subtracted in this inventive example, there is a case in which the subtraction is not necessary.

In addition, the Log Ratio value was calculated by $$\text{Log Ratio} = \text{Log}_2\{(FF-BF)/FM'\}.$$

The calculation was carried out on all spots.

Figure 6:
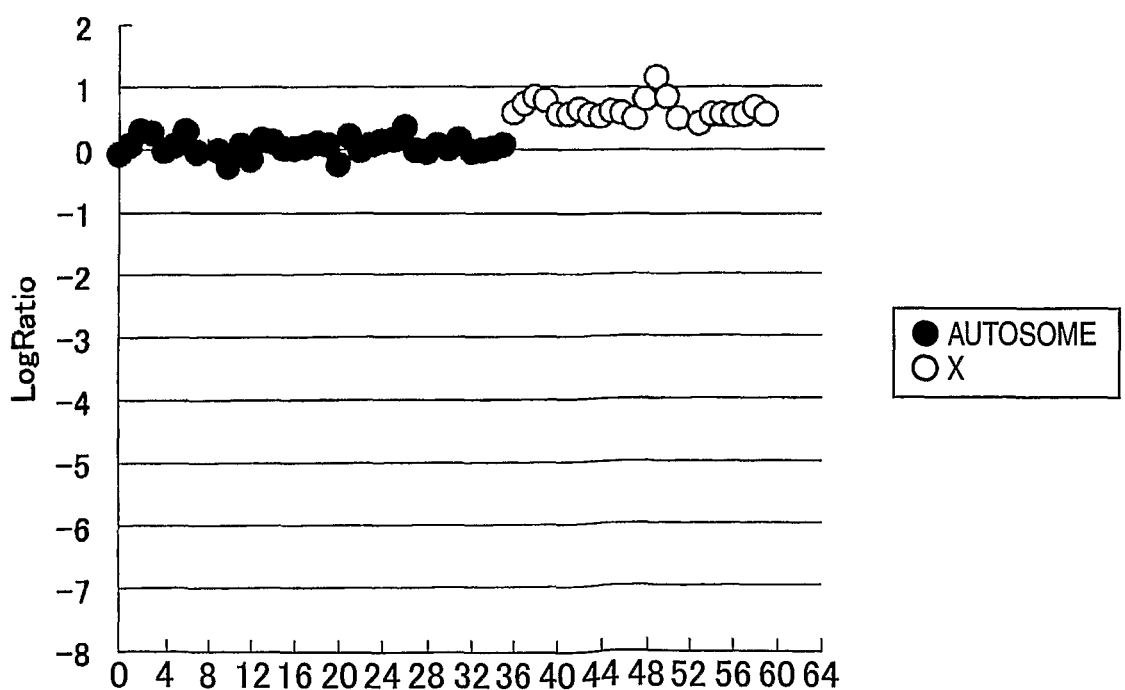
FIG. 6 is a result when un-purified labeled sample nucleic acid Cy 5-Female and un-purified labeled sample nucleic acid Cy 5-Male were used as the samples and corrected using Cy 3-Female as the labeled verification nucleic acid.

A difference in Log Ratio was obtained by calculating it in the same manner as in Comparative Example 1.
<Results>
Plotting of the Log Ratio is shown in FIG. 6.

In comparison with the case of not using a verification nucleic acid in FIG. 3, discrimination between autosome and X-chromosome is clear and the Log Ratio value is also put within a certain range, thus showing effectiveness of the use of a verification nucleic acid also in this inventive example.

Inventive Example 3

An Example of Correction when Log Ratio is Greatly Varied

<Preparation of Unpurified Labeled Nucleic Acid>

Respective unpurified labeled sample nucleic acids were prepared from a female-derived nucleic acid and a male-derived nucleic acid by the same method of Comparative Example 1.

<Preparation of Unpurified Labeled Verification Nucleic Acid>

An unpurified labeled verification nucleic acid Cy5-Cot-1 DNA was prepared using Cot-1 DNA as the verification nucleic acid.

<Preparation of Solution A>

Preparation of Solution a was Carried Out by the Same Method of Comparative Example 1.

<Preparation of Hybridization Solution>

Hybridization solutions containing an unpurified labeled sample nucleic acid and an unpurified labeled verification nucleic acid were prepared. That is, a hybridization solution containing unpurified labeled sample nucleic acid Cy3-Female and unpurified labeled verification nucleic acid Cy5-Cot-1 DNA, and a hybridization solution containing unpurified labeled sample nucleic acid Cy3-Male and unpurified labeled verification nucleic acid Cy5-Cot-1 DNA, were prepared.

<Pretreatment of Nucleic Acid Microarray>

This was carried out by the same method of the <Pretreatment of nucleic acid microarray> of Comparative Example 1.

In this case, a microarray of 1,600 spots consisting of two spots for each of 800 genes prepared from BAC clones, spotted at NGK INSULATORS, was used as the nucleic acid microarray.

<Hybridization>

Hybridization was carried out by the same method of the <Hybridization> of Comparative Example 1. In this case, a mixture of unpurified labeled sample nucleic acid Cy3-Female and unpurified labeled verification nucleic acid Cy5-Cot-1 DNA and a mixture of unpurified labeled sample nucleic acid Cy3-Male and unpurified labeled verification nucleic acid Cy5-Cot-1 DNA were respectively used as the sample.

<Washing of Nucleic Acid Microarray>

This was carried out by the same method of the <Washing of nucleic acid microarray> of Comparative Example 1.

<Data Uptake>

The thus washed two nucleic acid microarrays were subjected to scanning using GenePix 4000B (mfd. by Axon Instruments).

<Data Processing>

This was carried out in the same manner as in the <Data processing> of Inventive Example 1.

<Results>

Figure 8:
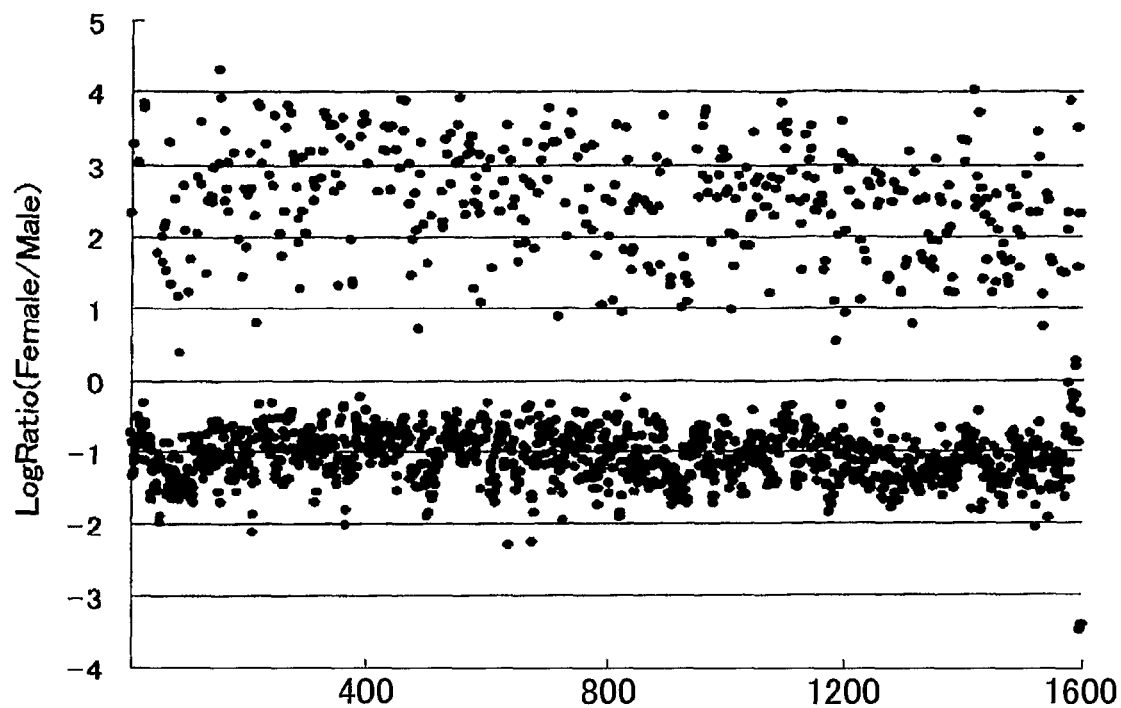
FIG. 8 is a result in which the Log Ratio calculated using fluorescence values of the sample Female and standard Male of FIGS. 7A and 7B was plotted in order of chromosomes.

Scanned images by this inventive example are shown in FIG. 8. Density of the image picture of the vertical row among right side of the right side drawing became thin.

Plotting of Log Ratio in the case of not carrying out correction using a verification nucleic acid is shown in FIG. 8.

Figure 9:
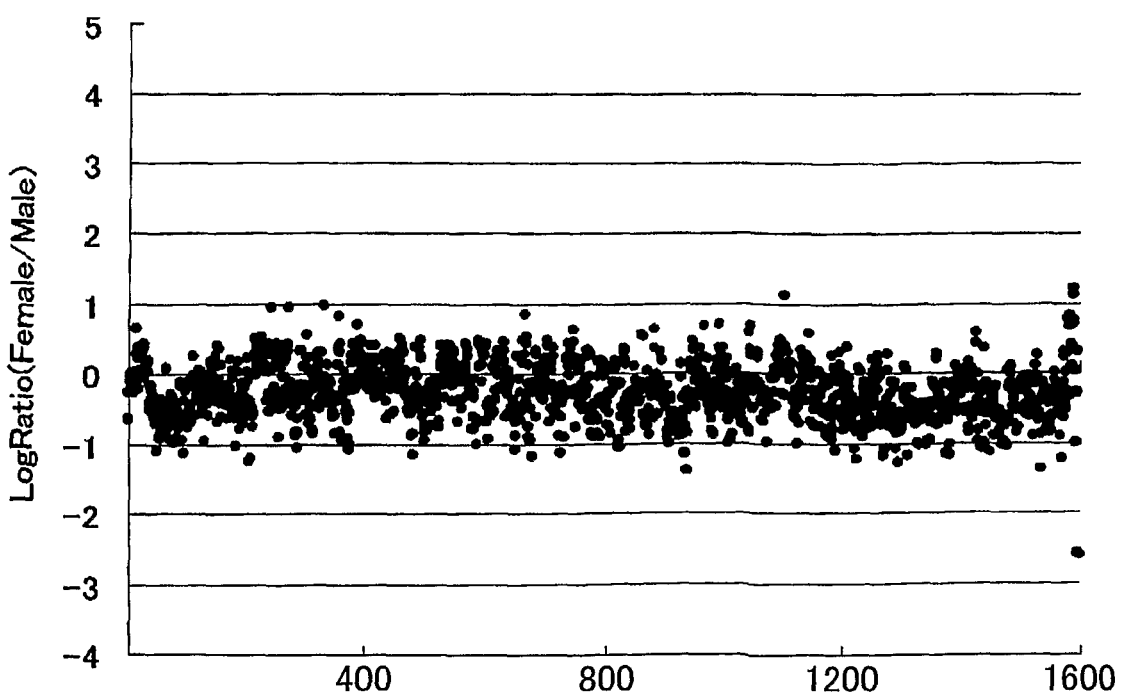
FIG. 9 is a result in which correction was carried out on the results of FIG. 8.

Plotting of Log Ratio in the case of carrying out correction of fluorescence values using a verification nucleic acid is shown in FIG. 9.

When FIG. 8 and FIG. 9 are compared, in the case of FIG. 8, it is considered that the thinness of read labeled quantity originated from the right side vertical row of the image drawing of FIG. 7B is the cause, and the Log Ratio values of spots in this region show values greatly different from the true value. However, contrary to this data, when the results of FIG. 9 in which the corrected values by the verification nucleic acid were included in the calculation formula are evaluated, it is clearly succeeded in reducing the data fluctuation.

Thus, the method of the invention exerts its power particularly when data greatly vary.

Inventive Example 4

Results when a Labeled Verification Nucleic Acid is Contained in the Hybridization Solution <Preparation of Unpurified Labeled Nucleic Acid>

Respective unpurified labeled sample nucleic acids were prepared from a female-derived nucleic acid and a male-derived nucleic acid by the same method of Comparative Example 1. In this connection, Cy3 was used in both cases.

<Preparation of Unpurified Labeled Verification Nucleic Acid>

An unpurified labeled verification nucleic acid Cy5-Cot-1 DNA was prepared by the same method of Inventive Example 1, using Cy5 as the labeling compound, and Cot-1 DNA as the verification nucleic acid.

<Preparation of a Solution Containing a Labeled Verification Nucleic Acid (Solution B)>

A 20 µl portion of the Cy5-Cot-1 DNA prepared in the <Preparation of unpurified labeled verification nucleic acid> and 65 µl (65 µg) of Cot-1 DNA were put into a 1.7 ml capacity micro tube and 8.5 µl of 3 M sodium acetate (pH 5.2) and 218 µl of ethanol cooled to −20° C. were added thereto and mixed therewith, and then the mixture was allowed to stand at −80° C. for 10 minutes. Thereafter, centrifugation was carried out at 4° C. and at 1,5000 rpm for 30 minutes using a centrifuge MX-300 manufactured by TOMY SEIKO. After the centrifugation, since the precipitate accumulated on the bottom of the centrifugation tube, the supernatant was discarded while taking care in not sucking the precipitate. Next, the remaining ethanol was removed by allowing the centrifugation tube to stand for 10 minutes while opening its cap. Ten minutes thereafter, 18 µl of 20% SDS was added thereto and allowed to stand for 30 minutes. After 30 minutes, 20 µl of a solution prepared by mixing and dissolving 1 g of dextran sulfate (mfd. by SIGMA), 5 ml of formamide and 1 ml of 20×SSC and then adjusting the liquid volume to 7 ml by adding water was added thereto, and the solution was and thoroughly mixed to obtain the solution B.

It is desirable that this step is not carried out by a user, but a kit producer prepares it in advance.

<Preparation of Hybridization Solution>

A 20 µl portion of the unpurified labeled sample nucleic acid Cy3-Female prepared in the <Preparation of unpurified labeled nucleic acid> and 58 µl of the solution B were put into a 1.7 ml capacity micro tube and sufficient stirring (Vortex) treatment was carried out. In addition, in the same manner, 20 µl of the unpurified labeled sample nucleic acid Cy3-Male prepared in the <Preparation of unpurified labeled nucleic acid> and 58 µl of the solution B were put into a 1.7 ml capacity micro tube and sufficient stirring (Vortex) treatment was carried out.

<Pretreatment of Nucleic Acid Microarray>

This was carried out by the same method of the <Pretreatment of nucleic acid microarray> of Comparative Example 1.

<Hybridization>

Figure 10:
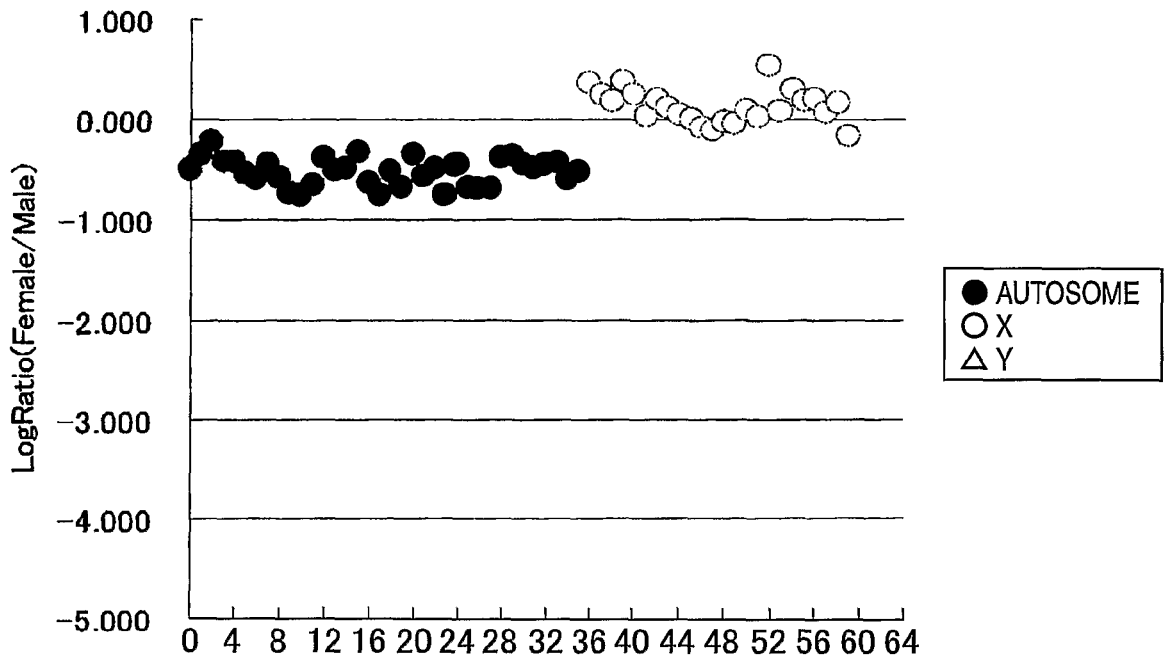
FIG. 10 is a result in which Female as the sample to be tested and Male as the standard were respectively used as samples.

Hybridization was carried out by the same method of the <Hybridization> of Comparative Example 1. In this case, a mixture of unpurified labeled sample nucleic acid Cy3-Female and unpurified labeled verification nucleic acid Cy5-Cot-1 DNA and a mixture of unpurified labeled sample nucleic acid Cy3-Male and unpurified labeled verification nucleic acid Cy5-Cot-1 DNA were respectively used as the sample.
<Washing of Nucleic Acid Microarray>
This was carried out by the same method of the <Washing of nucleic acid microarray> of Comparative Example 1.
<Data Uptake>
The thus washed two microarrays were subjected to scanning using GenePix 4000B (mfd. by Axon Instruments).
<Data Processing>
This was carried out in the same manner as in the <Data processing> of Inventive Example 1.
<Results>
Plotting of the Log Ratio of this inventive example is shown in FIG. 10.

The difference in Log Ratio became 0.644 which was improved by a factor of about 0.1 in comparison with the numerical value of 0.547 of the corrected result of FIG. 5 (Inventive Example 1), showing further improved ability as a nucleic acid microarray. It is considered that the cause of this is the effect of carrying out purification, because ethanol precipitation, namely purification, was carried out in the case of this inventive example after mixing of the unpurified labeled verification nucleic acid with the hybridization solution, while the unpurified labeled verification nucleic acid was directly added to the hybridization solution and stirred in the case of Inventive Example 1, and the liquid volume of the hybridization solution which was reduced by carrying out this ethanol precipitation, by a factor of 20 µl in comparison with the case of Inventive Example 1, namely the effect by the increase of nucleic acid concentration in the hybridization solution. In addition, the dispersion also became 0.134 which is smaller than the corrected result, 0.189, of FIG. 6, so that the ability as a nucleic acid microarray was further improved. It is considered that this is also the reason for the same cause.

Inventive Example 5

Using Amount-Dependency of Labeled Verification Nucleic Acid

<Preparation of Unpurified Labeled Nucleic Acid>
Respective unpurified labeled sample nucleic acids were prepared from a female-derived nucleic acid and a male-derived nucleic acid by the same method of Comparative Example 1.
<Preparation of Unpurified Labeled Verification Nucleic Acid>
Using Cy5 as the labeling compound and Cot-1 DNA as the verification nucleic acid, an unpurified labeled verification nucleic acid Cy5-Cot-1 DNA was prepared by the same method of Inventive Example 1. in this case, 3 µg of Cot-1 DNA was used as the Cot-1 DNA.
<Preparation of a Solution Containing a Labeled Verification Nucleic Acid>
This was carried out by the same method of the <Preparation of a solution containing a labeled verification nucleic acid> of Inventive Example 3.
<Preparation of Hybridization Solution>
This was carried out by the same method of the <Preparation of hybridization solution> of Inventive Example 3.
<Pretreatment of Nucleic Acid Microarray>
This was carried out by the same method of the <Pretreatment of nucleic acid microarray> of Comparative Example 1.

Figure 11:
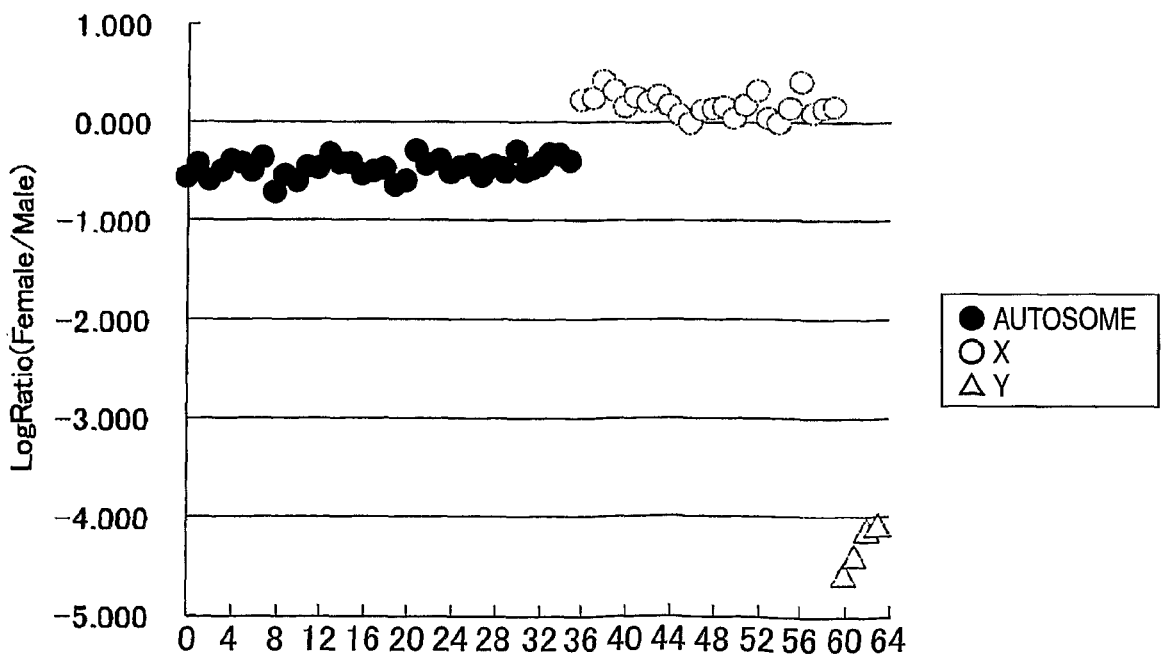
FIG. 11 is a result obtained using a further larger amount of Cot-1 than the case of FIG. 10 (8 times amount) as the material labeling it.

<Hybridization>
This was carried out by the same method of the <Hybridization> of Inventive Example 1.
<Washing of Nucleic Acid Microarray>
This was carried out by the same method of the <Washing of nucleic acid microarray> of Comparative Example 1.
<Data Uptake>
The thus washed two microarrays were subjected to scanning using GenePix 4000B (mfd. by Axon Instruments).
<Data Processing>
This was carried out in the same manner as in the <Data processing> of Inventive Example 1.
<Results>
Plotting of the Log Ratio in the case of carrying out correction of fluorescence values using the verification nucleic acid is shown in FIG. 11. In comparison with FIG. 10, the autosome converges further on 0. The difference in Log Ratio became 0.641 which was almost the same when compared with the value 0.644 which is a result (Inventive Example 4) of the case in which an unpurified labeled verification nucleic acid prepared using 0.75 µg of Cot-1 DNA as the stating material was used.

Inventive Example 6

Correction Between Different Array Formats

According to the invention, even when produce day, production method, production batch, plotting pattern, amount of immobilized probe nucleic acid and the like are different among arrays, their correction can be carried out when the same kind of probe nucleic acid is used. As an example thereof, an inventive example of a case having different plotting patterns on arrays, namely array formats, is shown in the following.
<Array 1> The array 1 is an array on which 4 spots for each of 16 genes, a total of 64 spots, are spotted. This is an array identical to the array used in Comparative Example 1 and the like.
<Array 2> The array 2 is a multiple test sample array on which 3 spots for each of 550 genes are spotted and which has two hybridization regions. In this connection, hybridization of the array 2 was carried out using a hybridizer.

In this inventive example, a comparison was carried out between 10 probe nucleic acids common in these two kinds of arrays using a verification nucleic acid. The 10 probes are 20p11.22, 20p12.3, 20p11.21, 21q22.3, 22q12.2, Xp11.23, Xp12, Xq13.3, Xq24 and Xq26.2.

Using a female DNA and a male DNA as the samples and using Cot-1 DNA as the verification nucleic acid, labeling of the samples, hybridization and data uptake were carried out by the same methods of other inventive examples. In this connection, though the array 2 is a multiple test sample array, the data from one hybridization region alone were used. In addition, though 4 spots of the same probe are spotted on the array 1, 3 of them were used in the comparison. Evaluation of the data was carried out by illustrating the Log Ratio using average of the 3 points.

Figure 12:
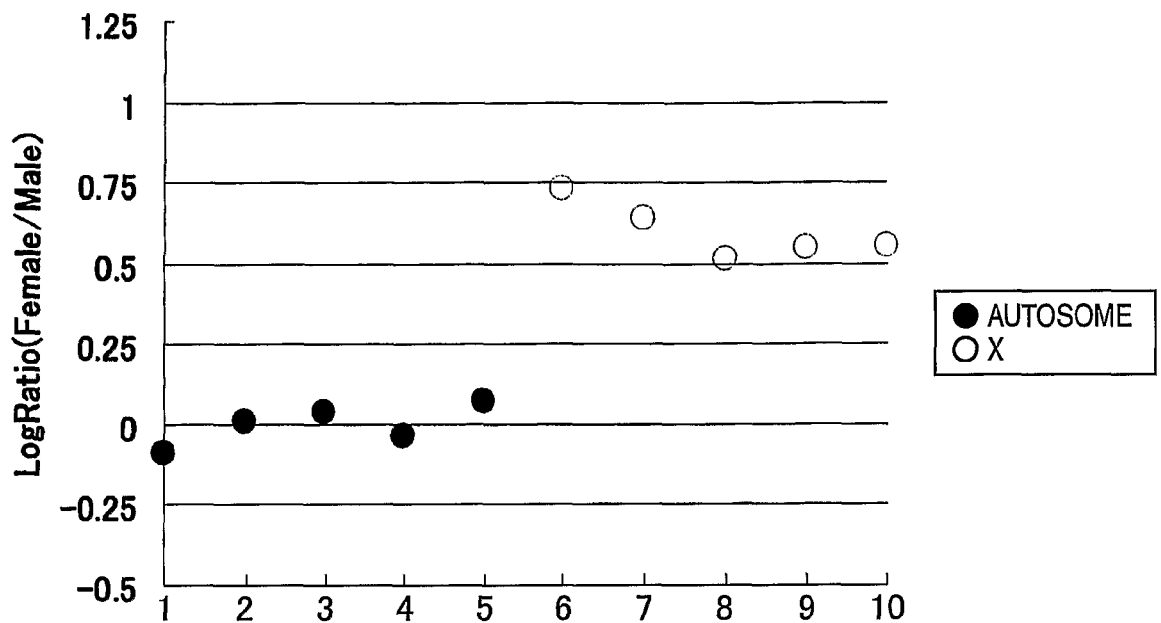
FIG. 12 is a result in which the correction was carried out between array 1.

FIG. 12 is a result of a case in which hybridization was carried out on two plates of the array 1, namely Cy3-Female DNA with Cy5-Cot-1 DNA on the first array, and Cy3-Male DNA with Cy5-Cot-1 DNA on the second array, and their correction was carried out by the method of the invention. As shown in the drawing, the autosomal moiety and the X-chromosomal moiety are sufficiently separated from each other.

Figure 13:
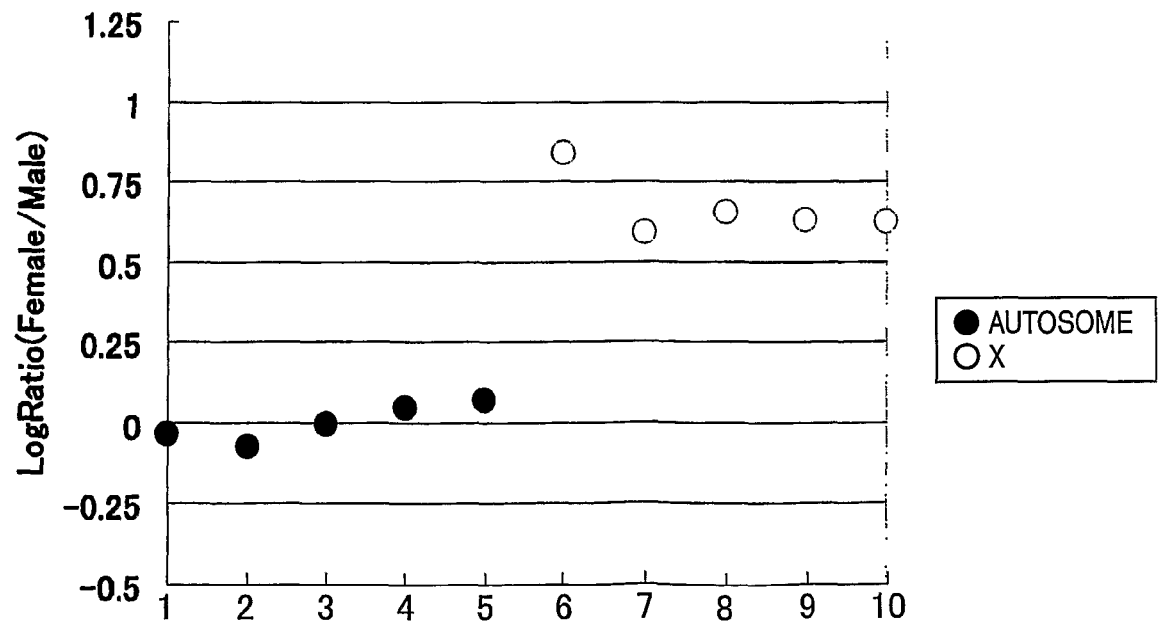
FIG. 13 is a result in which the correction was carried out between array 2.

FIG. 13 is a result of a case in which hybridization was carried out on two plates of the array 2, namely Cy3-Female DNA with Cy5-Cot-1 DNA on the first array, and Cy3-Male DNA with Cy5-Cot-1 DNA on the second array, and their correction was carried out by the method of the invention. As shown in the drawing, the autosomal moiety and the X-chromosomal moiety are sufficiently separated from each other also in this case.

Figure 14:
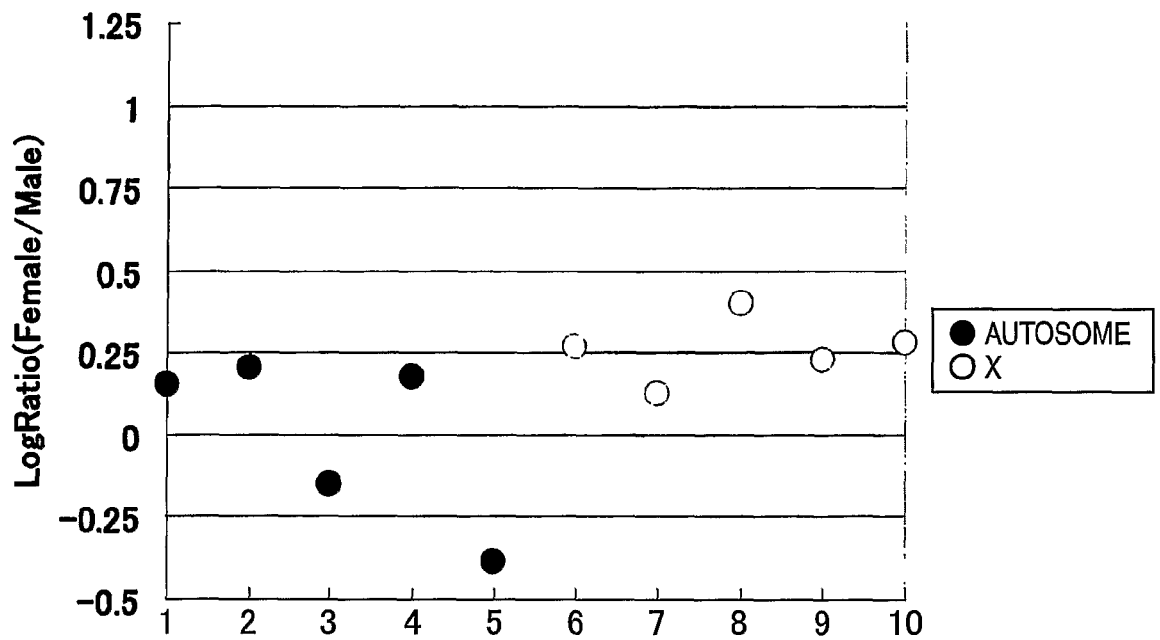
FIG. 14 is a result in which the array format was different and the correction was not carried out.

FIG. 14 is a result of a case in which hybridization was carried out on two plates using the array 1 and array 2, namely Cy3-Male DNA with Cy5-Cot-1 DNA on the first array, and Cy3-Female DNA with Cy5-Cot-1 DNA on the second array, and their correction was not carried out. As shown in the drawing, the autosomal moiety and X-chromosomal moiety are not separated from each other.

Figure 15:
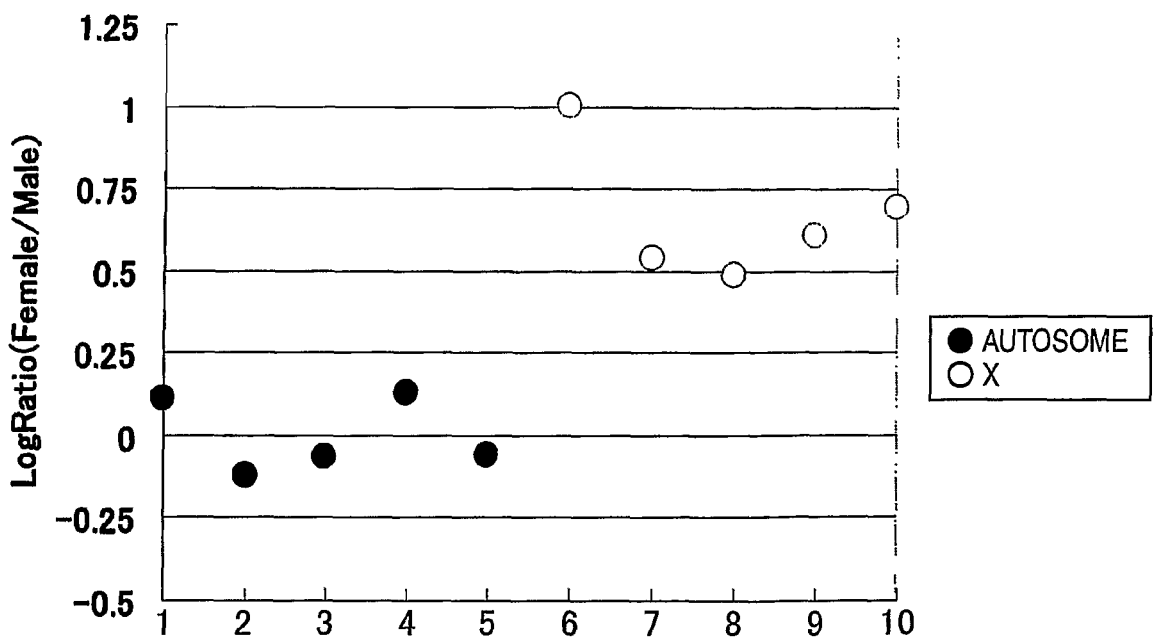
FIG. 15 is a result in which the array format was different and the correction was carried out.

FIG. 15 is a result of a case in which hybridization was carried out on two plates using the array 1 and array 2, namely Cy3-Male DNA with Cy5-Cot-1 DNA on the first array, and Cy3-Female DNA with Cy5-Cot-1 DNA on the second array, and their correction was carried out by the method of the invention. As shown in the drawing, the autosomal moiety and X-chromosomal moiety are sufficiently separated from each other. When compared with FIG. 14, it is shown that the use of a verification nucleic acid by the invention is a markedly effective method, because correction can be sufficiently carried out even when the array format is different. In addition, since the hybridization was carried out under different conditions, namely a manual static hybridization by a cover glass for the array 1 and a stirring type hybridization by a hybridizer for the array 2, these results show that their correction can be sufficiently carried out by the use of the method of the invention even when the hybridization conditions are different.

Inventive Example 7

Nucleic Acid Microarray in the Form of Providing Digital Data

<Preparation of unpurified labeled nucleic acid>, <Preparation of unpurified labeled verification nucleic acid>, <Preparation of a solution containing Cot-1 DNA>, <Preparation of hybridization solution>, <Pretreatment of nucleic acid microarray>, <Hybridization> and <Washing of nucleic acid microarray> were carried out by the same method of [Inventive Example 1]. In this case, a Cy3-Female DNA, supposing a normal cell-derived nucleic acid, and a labeled verification nucleic acid Cy5-Cot-1 DNA were used as the samples for digital data supplying data, these nucleic acids were hybridized on a nucleic acid microarray, and the data obtained therefrom were used as the data for digital data supplication use. On another day after the day of calculating this data, a Cy3-Male DNA, supposing an abnormal cell-derived nucleic acid, and a labeled verification nucleic acid Cy5-Cot-1 DNA (a sample completely identical to the aforementioned labeled verification nucleic acid Cy5-Cot-1 DNA was used) were hybridized on a nucleic acid microarray (which has the same probe and the same probe arrangement as those of the aforementioned nucleic acid microarray), and using this data and the aforementioned data, correction of the labeled quantity value of Cy3-Male DNA by both of the labeled verification nucleic acids was carried out in accordance with the <Data processing> of [Inventive Example 1].
<Results>

Figure 16:
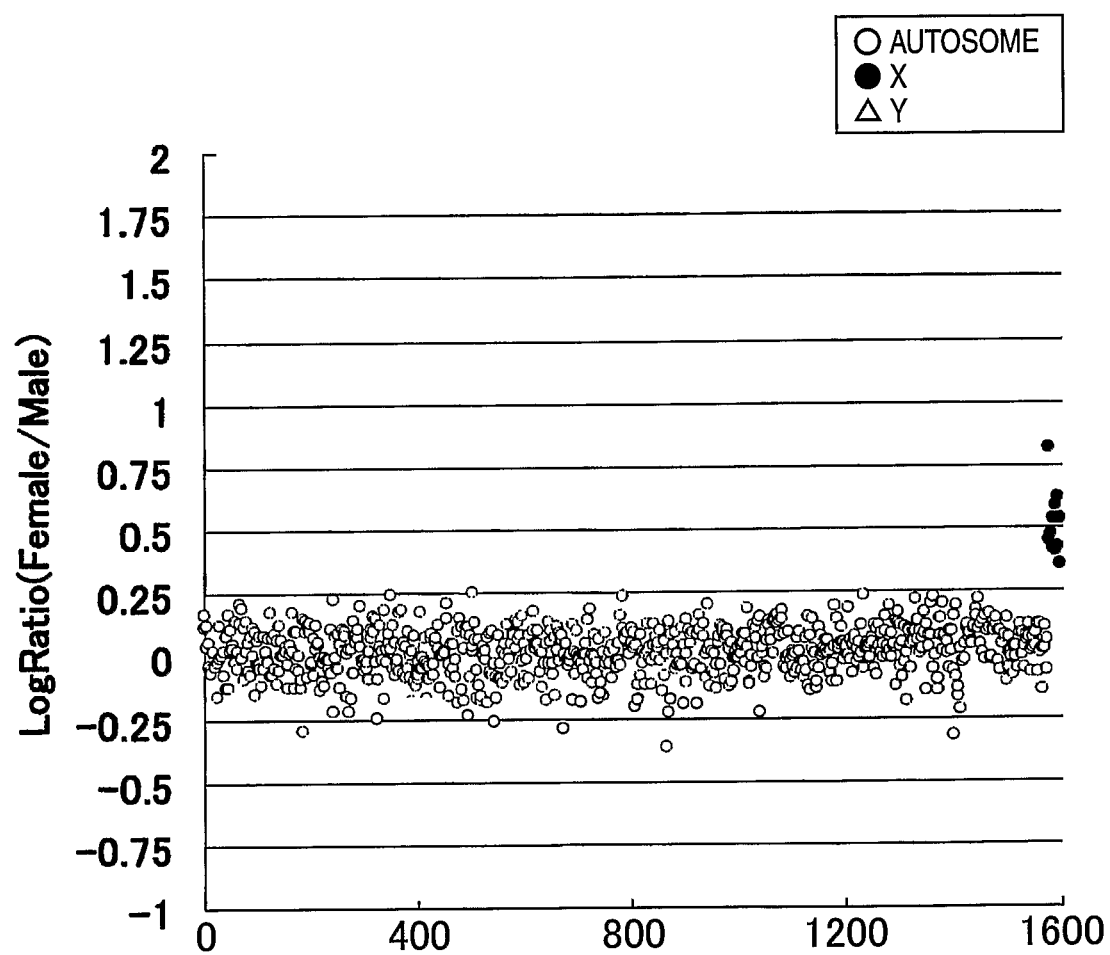
FIG. 16 is a result of a case in which the labeled quantity values were supplied as digital data.

The results are shown in FIG. 16. Data of the autosomal moiety converged on 0 point, and separation of the X-chromosomal moiety was also found sufficiently.

Inventive Example 8

Nucleic Acid Microarray Test and Analysis of a Case in Which a Vector-Derived Nucleic Acid was Used as the Verification Nucleic Acid <Preparation of Unpurified Labeled Nucleic Acid>

Respective unpurified labeled sample nucleic acids were prepared from a female-derived nucleic acid and a male-derived nucleic acid by the same method of Comparative Example 1. In this case, both of the female and male were labeled with Cy3.
<Preparation of Unpurified Labeled Verification Nucleic Acid>

In this inventive example, a vector-derived nucleic acid was used as the verification nucleic acid.
<Preparation of Verification Nucleic Acid>

One clone was selected from RPCI-11 and cultured overnight at 37° C. in LB medium which had been supplemented with chloramphenicol to a concentration of 100 mg/ml, using BE-43FL (mfd. by TAITEC). A BAC was extracted from this using QIAamp Miniprep kit manufactured by QIAgen. The thus extracted BAC was digested with a restriction enzyme NotI manufactured by Nippon Gene and subjected to an agarose electrophoresis. A fragment of about 7 kb was cut out and purified from the agarose using Nucleospin column manufactured by MN. Ligation of this was carried out at 4° C. overnight using T4 DNA ligase manufactured by Invitrogen, thereby obtaining pBAC108L.

The pBAC108L was added to DH-10B Chemical Competent Cell manufactured by Invitrogen, allowed to stand on ice for 30 minutes, heated at 42° C. for 30 seconds and again allowed to stand on ice for 2 minutes. This was mixed with 600 μl of SOC medium and spread on the LB medium containing 100 mg/ml of chloramphenicol using a spreader. After two nights of standing at 37° C., a colony thus grown was picked up and inoculated onto the LB medium containing 100 mg/ml of chloramphenicol. After overnight culturing of this at 37° C., a BAC DNA was extracted using QIAprep spin Miniprep kit manufactured by QIAgen, thereby obtaining a BAC vector. By labeling this using Cy5, a vector-derived labeled verification nucleic acid was obtained.
<Preparation of Solution A>

Preparation of Solution a was Carried Out by the Same Method of Comparative Example 1.
<Preparation of Hybridization Solution>

A 20 μl portion of the unpurified labeled sample nucleic acid Cy3-Female prepared by the same method of Inventive Example 1, 20 μl of the unpurified labeled verification nucleic acid Cy3-Female DNA prepared by the same method of Inventive Example 1 and 38 μl of the solution A were put into a 1.7 ml capacity micro tube and sufficient stirring (Vortex) treatment was carried out. In addition, in the same manner, 20 μl of the unpurified labeled sample nucleic acid Cy3-Male prepared in the <Preparation of unpurified labeled nucleic acid>, 20 μl of the vector-derived labeled verification nucleic acid prepared in the <Preparation of verification nucleic acid> and 380 of the solution A were put into a 1.7 ml capacity micro tube and sufficient stirring (Vortex) treatment was carried out.
<Pretreatment of Nucleic Acid Microarray>

This was carried out by the same method of the <Pretreatment of nucleic acid microarray> of Comparative Example 1.
<Hybridization>

Hybridization was carried out by the same method of the <Hybridization> of Comparative Example 1. In this case however, an HS-300 manufactured by ALOKA was used as the hybridization device. In addition, a mixture of the unpurified labeled sample nucleic acid Cy3-Female with the above-mentioned vector-derived labeled verification nucleic acid, and a mixture of the unpurified labeled sample nucleic acid Cy3-Male with the above-mentioned vector-derived labeled verification nucleic acid, were respectively used as two kinds of the sample.

<Washing of Nucleic Acid Microarray>

This was carried out by the same method of the <Washing of nucleic acid microarray> of Comparative Example 1.

<Data Uptake>

The thus washed two microarrays were subjected to scanning using GenePix 4000B (mfd. by Axon Instruments).

<Data Processing>

By regarding the unpurified labeled sample nucleic acid Cy3-Female-derived fluorescence value as FF, and the fluorescence value of the vector-derived labeled verification nucleic acid simultaneously hybridized with the unpurified labeled sample nucleic acid Cy3-Female as Fc1, the unpurified labeled sample nucleic acid Cy3-Male-derived fluorescence value as FM, and the fluorescence value of the vector-derived labeled verification nucleic acid simultaneously hybridized with the unpurified labeled sample nucleic acid Cy3-Male as Fc2, the values were calculated based on $Log_2$ (FM/Fc2/FF·Fc1) and arranged for each probe chromosome. In addition, the values of the same probe were averaged and made into a graph.

Figure 17:
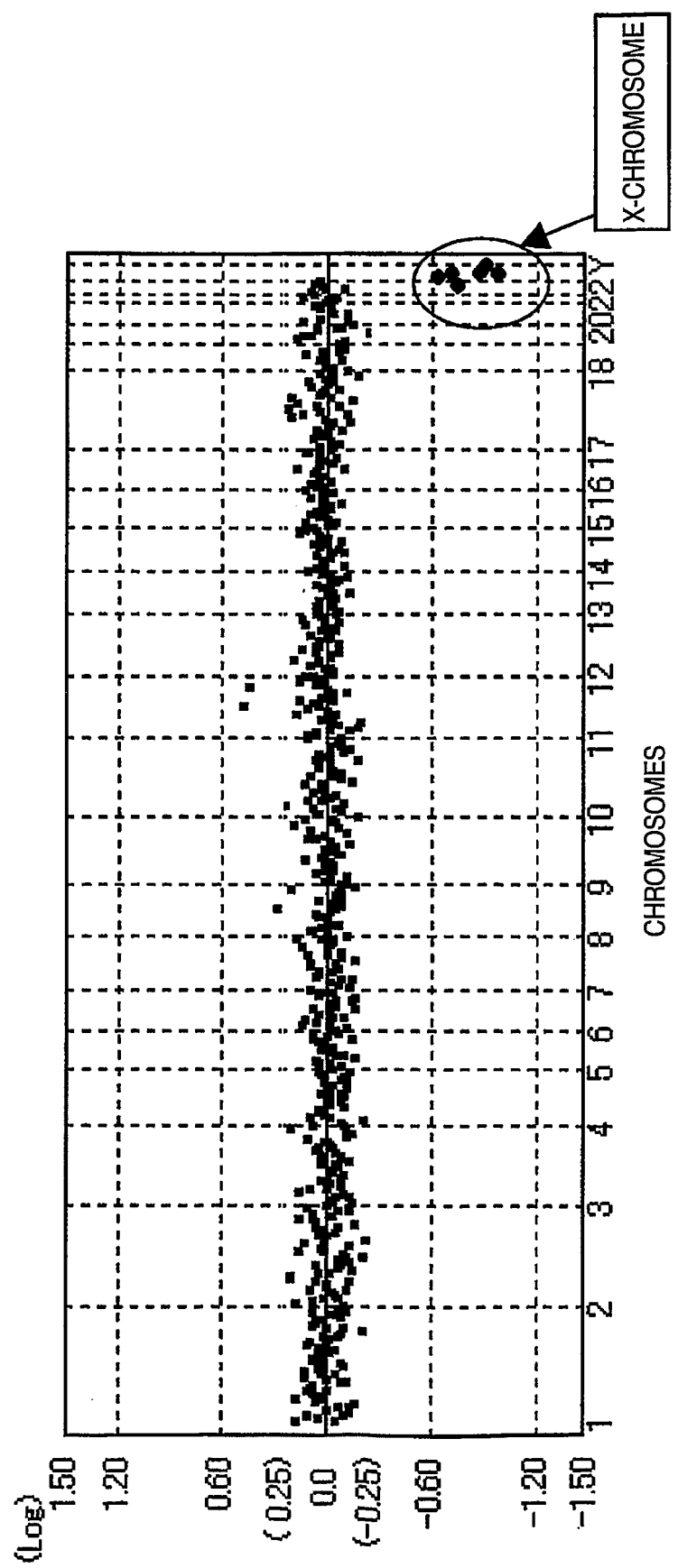
FIG. 17 is a result of a case in which a vector-derived nucleic acid was used as the verification nucleic acid.

The results are shown in FIG. 17. The value of $Log_2$ (FM/Fc2/FF·Fc1) was converged almost within ±0.25 in the case of the autosome and became a difference of almost 0.6 or more in the case of the X-chromosome, so that it was able to detect at a high sensitivity.

INDUSTRIAL APPLICABILITY

Though it is possible to get rid of a difference due to different labels by using the same label for the standard and sample to be tested, further use of a correction method aided with a labeled verification nucleic acid (B) has rendered possible get rid of a difference in spots between nucleic acid microarrays and high accuracy microarray measurement of nucleic acid. In addition, proper correction can be made by the use of the correction method of the invention even when spots are different, so far as the same probe is used. For example, even when the spotting amount of the probe nucleic acid and the arrangement and number of the spots are different, it further becomes possible to correct a difference due to a slight hybridization condition after hybridization.

Regarding the labeled verification nucleic acid (B) to be used in carrying out the correction, it was found also that further good results can be obtained by further increasing its desirable concentration in its labeling step.

This application is based on Japanese patent applications JP 2008-138533, filed on May 27, 2008 and JP 2009-126780, filed on May 26, 2009, the entire contents of which are hereby incorporated by reference, the same as if set forth at length.

The invention claimed is:

1. An analytical method aided with a nucleic acid microarray, the nucleic acid microarray having a spot (X 1) onto which a first probe nucleic acid is immobilized, the method comprising:

allowing a labeled sample nucleic acid (A 1) of a sample to be tested to hybridize with the first probe nucleic acid immobilized onto the spot (X 1);

providing the spot (X 1) with a labeled verification nucleic acid (B) that has a sequence capable of hybridizing with at least a part of the first probe nucleic acid and is labeled with a label different from the labeled sample nucleic acid (A 1), and allowing the labeled verification nucleic acid (B) to hybridize with at least the first probe nucleic acid at all spots;

measuring a labeled quantity value (F 1) of the labeled sample nucleic acid (A 1) hybridized on the spot (X 1); and measuring a labeled quantity value (Fc 1) of the labeled verification nucleic acid (B) hybridized on the spot (X 1), wherein the labeled verification nucleic acid (B) is a nucleic acid containing a repeated sequence, and wherein the nucleic acid containing a repeated sequence is Cot-1 DNA.

2. The analytical method according to claim 1, wherein the allowing of the labeled sample nucleic acid (A 1) to undergo hybridization and the allowing of the labeled verification nucleic acid (B) to undergo hybridization are simultaneously carried out, and the measuring of an amount of the hybridized labeled sample nucleic acid (A 1) and the measuring of an amount of the hybridized verification nucleic acid (B) are simultaneously carried out.

3. The analytical method according to claim 1, wherein an amount of the first probe nucleic acid immobilized onto the spot (X 1) is detected based on the labeled quantity value (Fc 1), and the labeled quantity value (F 1) is corrected based on the detected amount.

4. The analytical method according to claim 1, farther comprising:

providing a spot (X n) onto which an $n^{th}$ probe nucleic acid having the same sequence of the first probe nucleic acid immobilized onto the spot (X 1) with a labeled sample nucleic acid (A n) which is identical to or different from the labeled sample nucleic acid (A 1), and allowing the labeled sample nucleic acid (A n) to hybridize with the $n^{th}$ probe nucleic acid immobilized onto the spot (X n), the spot (X n) being present on the same nucleic acid microarray of the spot (X 1) or an another nucleic acid microarray;

providing the spot (X n) with the labeled verification nucleic acid (B), and allowing the labeled verification nucleic acid (B) to hybridize with at least the $n^{th}$ probe nucleic acid;

measuring a labeled quantity value (F n) of the labeled sample nucleic acid (A n) hybridized on the spot (X n); and measuring a labeled quantity value (Fc n) of the labeled verification nucleic acid (B) hybridized on the spot (X n).

5. The analytical method according to claim 4, further comprising:

calculating a coefficient of the labeled quantity values at the spot (X 1) and spot (X n) by comparing the labeled quantity values (Fc 1) and (Fc n).

6. The analytical method according to claim 4, wherein the labeled sample nucleic acid (A 1) and labeled sample nucleic acid (A n) are prepared by labeling nucleic acids obtained from different samples.

7. The analytical method according to claim 1, wherein an un-labeled nucleic acid identical to the same species of the labeled verification nucleic acid (B) before combining with a labeling compound is further added to the hybridization of the labeled verification nucleic acid (B).

8. The analytical method according to claim 4,
wherein a corrected labeled quantity value which corresponds to a hybridized amount of the labeled sample nucleic, acid (A n) on the spot (X n) is calculated by using the following formula (1):

$$\text{corrected labeled quantity value of the labeled sample nucleic acid } (A\,n) = \text{the labeled quantity value } (Fc\,1)/\text{the labeled quantity value } (Fc\,n) \times \text{the labeled quantity value } (F\,n) \text{ of the } n^{th} \text{ labeled sample nucleic acid } (A\,n) \; (n \text{ is an integer of 2 or more}) \qquad \text{formula (1).}$$

9. The analytical method according to claim 1,
wherein at least one labeling, of the labeled sample nucleic acid (A 1) and labeled verification nucleic acid (B) is effected by fluorescence.

10. The analytical method according to claim 1,
wherein a BAC-DNA microarray is used as the nucleic acid microarray.

11. The analytical method according to claim 1,
wherein two or more of the same species of the spots (X n) are present in different nucleic acid microarrays, and arrangement of the $n^{th}$ probe nucleic acid and spotting amounts of the $n^{th}$ probe nucleic acid between respective nucleic acid microarrays are different in respective nucleic acid microarrays.

12. The analytical method according to claim 1,
wherein a nucleic acid which is different from a nucleic acid of the sample and has a sequence on the first and $n^{th}$ probe nucleic acids is used as the labeled verification nucleic acid (B).

13. The analytical method according to claim 1, Wherein a vector-derived nucleic acid is used as the labeled verification nucleic acid (B).

14. The analytical method according to claim 1, wherein the labeled quantity value (Fc 1) among the labeled quantity values (F 1) and (Fc 1) is supplied by digital data.

* * * * *